United States Patent
Sosa et al.

(10) Patent No.: US 7,576,260 B2
(45) Date of Patent: Aug. 18, 2009

(54) NUCLEOTIDE SEQUENCES AND POLYPEPTIDES ENCODED THEREBY USEFUL FOR MODIFYING PLANT CHARACTERISTICS

(75) Inventors: Julissa Sosa, Northridge, CA (US); Greg Nadzan, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 349 days.

(21) Appl. No.: 11/140,347

(22) Filed: May 27, 2005

(65) Prior Publication Data

US 2006/0294622 A1 Dec. 28, 2006

Related U.S. Application Data

(60) Provisional application No. 60/575,309, filed on May 27, 2004.

(51) Int. Cl.
*C12N 15/82* (2006.01)
*A01H 5/00* (2006.01)
*A01H 5/10* (2006.01)

(52) U.S. Cl. .................. 800/278; 800/298; 435/419

(58) Field of Classification Search ................. None
See application file for complete search history.

(56) References Cited

U.S. PATENT DOCUMENTS

2004/0034888 A1 2/2004 Liu et al.
2006/0294622 A1* 12/2006 Sosa et al. .................. 800/286

FOREIGN PATENT DOCUMENTS

EP 10333405 A2 * 9/2000

OTHER PUBLICATIONS

Wells (Biochemistry 29:8509-8517, 1990).*
Ngo et al., (The Protein Folding Problem and Tertiary Structure Prediction, K. Merz., and S. Le Grand (eds.) pp. 492-495, 1994).*
Keskin et al. (Protein Science, 13:1043-1055, 2004).*
Thornton et al. (Nature structural Biology, structural genomics supplement, Nov. 2000).*
Dai et al. (Plant Physiol. 144:121-133, 2007).*
Database Geneseq [Online] Oct. 17, 2000, "*Arabidopsis thaliana* protein fragment SEQ ID No. 2185," XP002398578, Retrieved from EBI accession No. GSP:AAG05688, Database accession No. AAG05688, the whole document & EP 1 033 405 A (Ceres Incorporated), Sep. 6, 2000.
Database Geneseq [Online] May 31, 2002, "Herbicidally active polypeptide SEQ ID No. 933," XP002398579, retrieved from EBI accession No. GSP:ABB91722, Database accession No. ABB91722, the whole document & WO 02/10210 A (Bayer Aktiengesellschaft; Tietjen, Klaus; Weidler, Marcus) Feb. 7, 2002.
Wi, Soo Jin et al., "Antisense expression of carnation cDNA encoding ACC synthase or ACC oxidase enhances polyamine content and abiotic stress tolerance in transgenic tobacoo plants," Moelcules and Cells, Seoul, KR, vol. 13, No. 2, Apr. 30, 2002, pp. 209-220, XP002338203.

* cited by examiner

*Primary Examiner*—Cynthia Collins
(74) *Attorney, Agent, or Firm*—Birch, Stewart, Kolasch & Birch, LLP

(57) ABSTRACT

Isolated polynucleotides and polypeptides encoded thereby are described, together with the use of those products for making transgenic plants with increased tolerance to pH or increased phosphorus efficiency.

3 Claims, 2 Drawing Sheets

Figure 1. Diagram showing the relationships between soil minerals and pH.
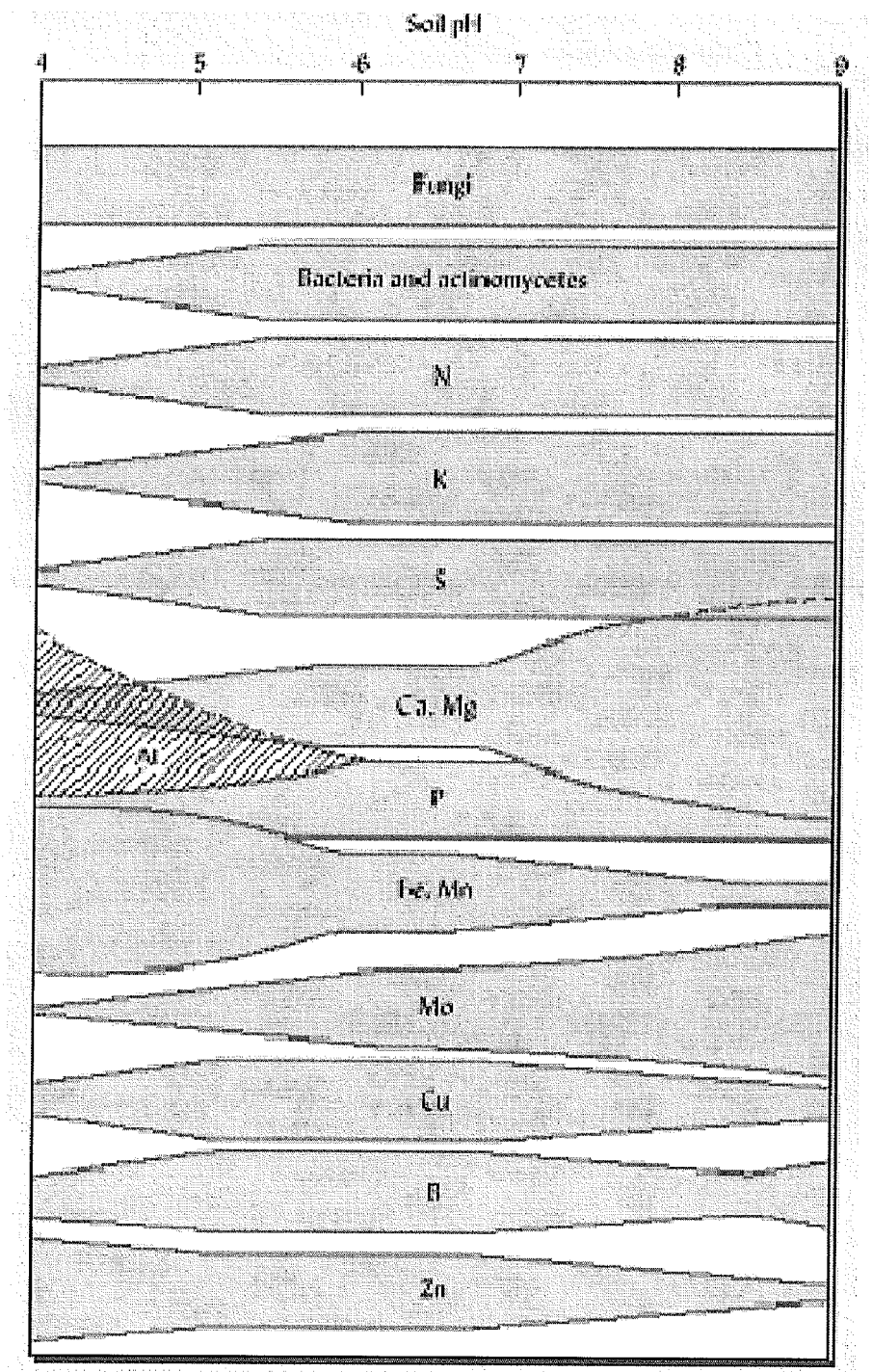

Figure 2. pH recovery assessment as determined by volume of seeds collected from SP5pH8 candidate containing clone 126592 in comparison to pH treated and untreated controls.
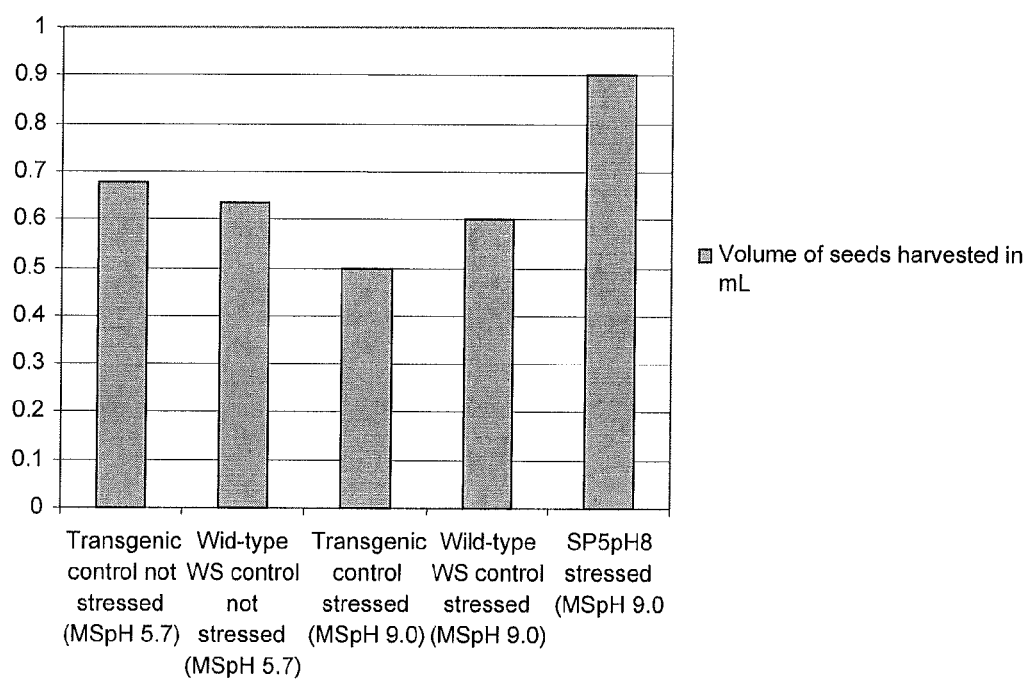

```
                          SEQUENCE LISTING

<160> NUMBER OF SEQ ID NOS: 49

<210> SEQ ID NO 1
<211> LENGTH: 618
<212> TYPE: DNA
<213> ORGANISM: Arabidopsis thaliana
<220> FEATURE:
<221> NAME/KEY: misc_feature
<223> OTHER INFORMATION: clone34035_inplanta_experimental_L42

<400> SEQUENCE: 1
gcttaaagtc tctggtcaaa tgggaaatag tgtaagaagc aatctaagag acatcagagg      60
acgacgatcg atggatcctc ggatgtggca caaagtcgcc gctatttccg gtatggctgc     120
tcttggtttg ggaacttatg gtgctcatgt ctttaaacca gagaacccct cttacaaaca     180
ggtgtggcaa acggcttcac tttaccattt ggttcacact gctgctcttg tttctgctcc     240
tagcaccaaa tatcccaaca tttttggtgg cttgttgact gctggaattg tagccttttc     300
cggcacgtgt tatatggtag cgctgcggga ggacagaaag ttttcgacat tggcaccatt     360
cggaggcttt gcgttcattg ctgcatgggc aactttactt ttctaaacaa tctcataacc     420
atctatattg tcaagtttgt ggtcaagctt atcctacata tgaactcact gttttttttt     480
gtttacctaa gagattgctt aataacaatt ctgtgtcgac aaccattaag catcttcctt     540
tacttgttca gtttgttgct aaaggggatta tgtaaatgac gaccatatta atgtaatctt     600
attaccatac aatttacc                                                    618

<210> SEQ ID NO 2
<211> LENGTH: 128
<212> TYPE: PRT
<213> ORGANISM: Arabidopsis thaliana
<220> FEATURE:
<221> NAME/KEY: misc_feature
<223> OTHER INFORMATION: peptide_clone34035_inplanta_experimental_L42

<400> SEQUENCE: 2

Met Gly Asn Ser Val Arg Ser Asn Leu Arg Asp Ile Arg Gly Arg Arg
1               5                   10                  15

Ser Met Asp Pro Arg Met Trp His Lys Val Ala Ala Ile Ser Gly Met
            20                  25                  30

Ala Ala Leu Gly Leu Gly Thr Tyr Gly Ala His Val Phe Lys Pro Glu
        35                  40                  45

Asn Pro Ser Tyr Lys Gln Val Trp Gln Thr Ala Ser Leu Tyr His Leu
    50                  55                  60

Val His Thr Ala Ala Leu Val Ser Ala Pro Ser Thr Lys Tyr Pro Asn
65                  70                  75                  80

Ile Phe Gly Gly Leu Leu Thr Ala Gly Ile Val Ala Phe Ser Gly Thr
                85                  90                  95

Cys Tyr Met Val Ala Leu Arg Glu Asp Arg Lys Phe Ser Thr Leu Ala
            100                 105                 110
```

```
Pro Phe Gly Gly Phe Ala Phe Ile Ala Ala Trp Ala Thr Leu Leu Phe
        115                 120                 125

<210> SEQ ID NO 3
<211> LENGTH: 111
<212> TYPE: PRT
<213> ORGANISM: Brassica napus
<220> FEATURE:
<221> NAME/KEY: misc_feature
<223> OTHER INFORMATION: CeresClone:872428

<400> SEQUENCE: 3

Met Asp Pro Arg Ile Trp His Lys Val Ala Ala Val Ser Gly Met Ala
1               5                   10                  15

Ala Leu Gly Leu Gly Thr Tyr Gly Ala His Val Phe Lys Pro Glu Asn
            20                  25                  30

Pro Ser Tyr Lys Gln Val Trp Gln Thr Ala Ser Leu Tyr His Leu Val
        35                  40                  45

His Thr Ala Ala Leu Val Ser Ala Pro Ser Thr Lys Tyr Pro Asn Ile
50                  55                  60

Phe Gly Gly Leu Leu Thr Ala Gly Ile Val Ala Phe Ser Gly Thr Cys
65                  70                  75                  80

Tyr Met Val Ala Leu Arg Glu Asp Arg Lys Phe Ser Thr Leu Ala Pro
                85                  90                  95

Phe Gly Gly Phe Ala Phe Ile Ala Ala Trp Ala Thr Leu Leu Phe
            100                 105                 110

<210> SEQ ID NO 4
<211> LENGTH: 113
<212> TYPE: PRT
<213> ORGANISM: Brassica napus
<220> FEATURE:
<221> NAME/KEY: misc_feature
<223> OTHER INFORMATION: CeresClone:972918

<400> SEQUENCE: 4

Met Gly Asn Cys Val Arg Ser Asn Leu Arg Leu Gly Gly Arg Arg
1               5                   10                  15

Ser Met Asp Pro Arg Ile Trp His Lys Val Ala Ala Val Ser Gly Met
            20                  25                  30

Ala Ala Leu Gly Leu Gly Thr Tyr Gly Ala His Val Phe Lys Pro Glu
        35                  40                  45

Asn Pro Ser Tyr Lys Gln Val Trp Gln Thr Ala Ser Leu Tyr His Leu
    50                  55                  60

Val His Thr Ala Ala Leu Val Ser Ala Pro Ser Thr Lys Tyr Pro Asn
65                  70                  75                  80

Ile Phe Gly Gly Leu Leu Thr Ala Gly Ile Val Ala Phe Ser Gly Thr
                85                  90                  95

Tyr Glu Tyr Ala Lys Ser Phe Val Phe Val Asn Val Val Gly Val Thr
            100                 105                 110

Trp

<210> SEQ ID NO 5
<211> LENGTH: 111
<212> TYPE: PRT
<213> ORGANISM: Glycine max
<220> FEATURE:
<221> NAME/KEY: misc_feature
<223> OTHER INFORMATION: CeresClone:566573
```

<400> SEQUENCE: 5

```
Met Asp Pro Gln Leu Trp His Lys Val Ala Ala Ile Ser Gly Leu Ala
1               5                   10                  15

Ala Leu Gly Leu Gly Thr Tyr Gly Ala His Val Phe Lys Pro Gln Asn
            20                  25                  30

Pro Ala Tyr Asn Asp Val Trp His Thr Ala Ser Leu Tyr His Leu Val
        35                  40                  45

His Thr Ala Ala Leu Val Ala Ala Pro Ile Thr Lys His Pro Asn Val
    50                  55                  60

Phe Gly Gly Leu Leu Thr Ala Gly Ile Leu Ala Phe Ser Gly Thr Cys
65                  70                  75                  80

Tyr Thr Val Ala Phe Leu Glu Asp Arg Lys Tyr Ser Thr Met Ala Pro
                85                  90                  95

Phe Gly Gly Phe Ala Phe Ile Ala Ala Trp Gly Ser Leu Phe Phe
            100                 105                 110
```

<210> SEQ ID NO 6
<211> LENGTH: 111
<212> TYPE: PRT
<213> ORGANISM: Glycine max
<220> FEATURE:
<221> NAME/KEY: misc_feature
<223> OTHER INFORMATION: CeresClone:588155

<400> SEQUENCE: 6

```
Met Asp Pro Gln Val Trp His Lys Val Ala Ala Ile Ser Gly Val Ala
1               5                   10                  15

Ala Leu Gly Leu Gly Thr Tyr Gly Ala His Val Phe Lys Pro Gln Asn
            20                  25                  30

Pro Ala Tyr Lys Asp Val Trp His Thr Ala Ser Leu Tyr His Leu Val
        35                  40                  45

His Thr Ala Ala Leu Val Ala Ala Pro Ile Thr Lys His Pro Asn Val
    50                  55                  60

Phe Gly Gly Leu Leu Thr Ala Gly Ile Leu Ala Phe Ser Gly Thr Cys
65                  70                  75                  80

Tyr Thr Val Ala Phe Leu Glu Asp Arg Lys Tyr Ser Thr Met Ala Pro
                85                  90                  95

Phe Gly Gly Phe Ala Phe Ile Ala Ala Trp Gly Ser Leu Phe Phe
            100                 105                 110
```

<210> SEQ ID NO 7
<211> LENGTH: 115
<212> TYPE: PRT
<213> ORGANISM: Triticum aestivum
<220> FEATURE:
<221> NAME/KEY: misc_feature
<223> OTHER INFORMATION: CeresClone:678257

<400> SEQUENCE: 7

```
Met Val Met Pro Thr Asp Pro Met Leu Trp His Lys Val Ala Ala Val
1               5                   10                  15

Ser Gly Val Val Ala Leu Gly Leu Gly Thr Tyr Gly Ala His Met Phe
            20                  25                  30

Arg Pro Gln Asn Pro Arg Tyr Lys Glu Ile Trp Gln Thr Ala Ser Leu
        35                  40                  45

Tyr His Leu Val His Thr Ala Ala Leu Leu Gly Ala Pro Met Thr Lys
    50                  55                  60

Arg Pro Asn Ile Phe Gly Gly Leu Leu Thr Thr Gly Ile Val Leu Phe
```

```
                65                  70                  75                  80
Ser Gly Thr Cys Tyr Thr Val Ala Tyr Leu Glu Asp Arg Lys Phe Ser
                    85                  90                  95
Ser Pro Ala Pro Ile Gly Gly Phe Ala Phe Ile Ala Ala Trp Ala Ser
                100                 105                 110
Leu Leu Phe
        115

<210> SEQ ID NO 8
<211> LENGTH: 115
<212> TYPE: PRT
<213> ORGANISM: Zea mays
<220> FEATURE:
<221> NAME/KEY: misc_feature
<223> OTHER INFORMATION: CeresClone:289088

<400> SEQUENCE: 8

Met Leu Ala Ala Thr Asp Pro Met Leu Trp His Lys Val Ala Val
1               5                   10                  15
Ser Gly Val Ala Ala Leu Gly Leu Gly Thr Tyr Gly Ala His Met Phe
                20                  25                  30
Arg Pro Lys Asn Pro Ala Tyr Lys Glu Val Trp His Thr Ala Ser Leu
            35                  40                  45
Tyr His Leu Val His Thr Ala Ala Leu Leu Gly Ala Pro Ile Thr Lys
        50                  55                  60
Arg Pro Asn Val Phe Gly Gly Leu Leu Thr Ala Gly Ile Val Leu Phe
65                  70                  75                  80
Ser Gly Thr Cys Tyr Thr Val Ala Tyr Leu Glu Asp Arg Lys Phe Ser
                    85                  90                  95
Ser Pro Ala Pro Leu Gly Gly Phe Ala Phe Ile Ala Ala Trp Ala Ser
                100                 105                 110
Leu Leu Phe
        115

<210> SEQ ID NO 9
<211> LENGTH: 93
<212> TYPE: PRT
<213> ORGANISM: Psathyrostachys juncea
<220> FEATURE:
<221> NAME/KEY: misc_feature
<223> OTHER INFORMATION: gi[79]63694

<400> SEQUENCE: 9

Met Leu Trp His Lys Val Ala Ala Val Ser Gly Val Ala Ala Leu Gly
1               5                   10                  15
Leu Gly Thr Tyr Gly Ala His Met Phe Arg Pro Gln Asn Pro Lys Tyr
                20                  25                  30
Lys Glu Ile Trp Gln Thr Ala Phe Leu Tyr His Leu Val His Thr Ala
            35                  40                  45
Ala Leu Leu Gly Ala Pro Met Thr Lys Arg Pro Asn Ile Phe Gly Gly
        50                  55                  60
Leu Leu Thr Thr Gly Ile Val Leu Phe Ser Gly Thr Cys Tyr Thr Val
65                  70                  75                  80
Ala Tyr Leu Glu Asp Arg Lys Phe Ser Ser Pro Ala Pro
                    85                  90

<210> SEQ ID NO 10
<211> LENGTH: 106
<212> TYPE: PRT
```

<213> ORGANISM: Agropyron cristatum
<220> FEATURE:
<221> NAME/KEY: misc_feature
<223> OTHER INFORMATION: gi[79]63702

<400> SEQUENCE: 10

Met Val Met Pro Thr Asp Pro Met Leu Trp His Lys Val Ala Ala Val
1               5                   10                  15

Ser Gly Val Ala Ala Leu Gly Leu Gly Thr Tyr Gly Ala His Met Phe
            20                  25                  30

Arg Pro Gln Asn Pro Arg Tyr Lys Glu Ile Trp Gln Thr Ala Ser Leu
        35                  40                  45

Tyr His Leu Val His Thr Ala Ala Leu Leu Gly Ala Pro Met Thr Lys
    50                  55                  60

Arg Pro Asn Ile Phe Gly Leu Leu Thr Thr Gly Ile Val Leu Phe
65                  70                  75                  80

Ser Gly Thr Cys Tyr Thr Val Ala Tyr Leu Glu Asp Arg Lys Phe Ser
                85                  90                  95

Ser Pro Ala Pro Ile Gly Gly Phe Ala Phe
            100                 105

<210> SEQ ID NO 11
<211> LENGTH: 120
<212> TYPE: PRT
<213> ORGANISM: Oryza sativa subsp. japonica
<220> FEATURE:
<221> NAME/KEY: misc_feature
<223> OTHER INFORMATION: gi[50]918749

<400> SEQUENCE: 11

Met Ala Ala Ala Ala Met Ala Met Lys Asp Pro Ser Leu Trp His
1               5                   10                  15

Lys Val Ala Ala Ile Ser Gly Val Ala Ala Leu Gly Leu Gly Thr Tyr
            20                  25                  30

Gly Ala His Met Phe Arg Pro Lys Asn Pro Ala Tyr Lys Glu Val Trp
        35                  40                  45

His Thr Ala Ser Leu Tyr His Leu Val His Thr Ala Ala Leu Leu Gly
    50                  55                  60

Ala Pro Ile Thr Lys Arg Pro Asp Val Phe Gly Gly Leu Leu Thr Ala
65                  70                  75                  80

Gly Ile Val Leu Phe Ser Gly Thr Cys Tyr Thr Val Ala Tyr Leu Glu
                85                  90                  95

Asp Arg Lys Tyr Ser Ser Thr Ala Pro Leu Gly Gly Phe Ala Phe Ile
            100                 105                 110

Ala Ala Trp Ala Ser Leu Leu Phe
        115                 120

<210> SEQ ID NO 12
<211> LENGTH: 689
<212> TYPE: DNA
<213> ORGANISM: Arabidopsis thaliana
<220> FEATURE:
<221> NAME/KEY: misc_feature
<223> OTHER INFORMATION: clone40781_inplanta_experimental_L43

<400> SEQUENCE: 12
ataaacgaat ccaaatttca agaggagaag aaaaatcttc aagtccacga cgaaactttt      60
catcgatctt caaattccag aaaaaactcg atgaatcttc aagctgtttc ttgtagcttc     120
ggattccttt cgagtccact tggtgtcact cccagaactt cgtttcgtcg cttcgtaatc     180

-continued

```
cgagcgaaaa cggaaccgtc ggagaaatca gtagagatta tgaggaaatt ctccgagcaa      240
tatgctcgtc gctctgggac ttacttctgt gttgataaag gagttacttc agtcgttatt      300
aagggtttgg ctgagcataa agattcatat ggtgcaccgc tttgcccttg cagacactat      360
gatgataaag ctgctgaggt tggacaaggc ttttggaatt gtccgtgtgt tccaatgaga      420
gagaggaagg agtgccattg tatgcttttc ttaactcctg ataatgattt cgctggaaaa      480
gatcagacga ttcatcgga tgaaataaaa gaaactacag ctaacatgtg agagagctgg      540
ttcttccatg ttcatcacct ctgttcttta ggtaaaaaaa aagagagata tgtctcgccc      600
caaatgcagt cttgtacatt gatacccga gcatcttctt cgttcttctg tacaactctt      660
tcactcttaa gataatattc tttagtatg                                        689
```

<210> SEQ ID NO 13
<211> LENGTH: 146
<212> TYPE: PRT
<213> ORGANISM: Arabidopsis thaliana
<220> FEATURE:
<221> NAME/KEY: misc_feature
<223> OTHER INFORMATION: peptide_clone40781_inplanta_experimental_L43

<400> SEQUENCE: 13

```
Met Asn Leu Gln Ala Val Ser Cys Ser Phe Gly Phe Leu Ser Ser Pro
1               5                   10                  15

Leu Gly Val Thr Pro Arg Thr Ser Phe Arg Arg Phe Val Ile Arg Ala
            20                  25                  30

Lys Thr Glu Pro Ser Glu Lys Ser Val Glu Ile Met Arg Lys Phe Ser
        35                  40                  45

Glu Gln Tyr Ala Arg Arg Ser Gly Thr Tyr Phe Cys Val Asp Lys Gly
    50                  55                  60

Val Thr Ser Val Val Ile Lys Gly Leu Ala Glu His Lys Asp Ser Tyr
65                  70                  75                  80

Gly Ala Pro Leu Cys Pro Cys Arg His Tyr Asp Asp Lys Ala Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile His Arg Ser Asp Glu Ile Lys Glu Thr Thr Ala
    130                 135                 140

Asn Met
145
```

<210> SEQ ID NO 14
<211> LENGTH: 148
<212> TYPE: PRT
<213> ORGANISM: Spinacia oleracea
<220> FEATURE:
<221> NAME/KEY: misc_feature
<223> OTHER INFORMATION: gi[50]5189

<400> SEQUENCE: 14

```
Met Lys Ala Leu Gln Ala Ser Thr Ser Tyr Ser Phe Phe Ser Lys Ser
1               5                   10                  15

Ser Ser Ala Thr Leu Gln Arg Arg Thr His Arg Pro Gln Cys Val Ile
            20                  25                  30

Leu Ser Lys Val Glu Pro Ser Asp Lys Ser Val Glu Ile Met Arg Lys
        35                  40                  45
```

```
Phe Ser Glu Gln Tyr Ala Arg Lys Ser Gly Thr Tyr Phe Cys Val Asp
        50                  55                  60

Lys Gly Val Thr Ser Val Val Ile Lys Gly Leu Ala Glu His Lys Asp
65                  70                  75                  80

Ser Leu Gly Ala Pro Leu Cys Pro Cys Arg Tyr Tyr Asp Asp Lys Ala
                85                  90                  95

Ala Glu Ala Thr Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Lys Asp Gln Thr Ile Gly Leu Asp Glu Ile Arg Glu Val
    130                 135                 140

Thr Ala Asn Met
145

<210> SEQ ID NO 15
<211> LENGTH: 143
<212> TYPE: PRT
<213> ORGANISM: Brassica napus
<220> FEATURE:
<221> NAME/KEY: misc_feature
<223> OTHER INFORMATION: CeresClone:1127455
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid

<400> SEQUENCE: 15

Met Asn Pro Gln Ala Val Ser Cys Ser Phe Gly Phe Val Ser Ala Pro
1               5                   10                  15

Leu Val Ser Pro Arg Thr Ser Arg Phe Val Val Gln Ala Lys Ser Glu
            20                  25                  30

Pro Ser Glu Xaa Ser Val Glu Ile Met Arg Lys Phe Ser Glu Gln Tyr
        35                  40                  45

Ala Arg Arg Ser Gly Thr Tyr Phe Cys Val Asp Lys Gly Val Xaa Ser
    50                  55                  60

Val Val Ile Lys Gly Leu Ala Glu His Lys Asp Ser Tyr Gly Ala Pro
65                  70                  75                  80

Leu Cys Pro Cys Arg His Tyr Asp Asp Lys Ala Ala Glu Val Gly Gln
                85                  90                  95

Gly Phe Trp Asn Cys Pro Cys Val Pro Met Arg Glu Arg Lys Glu Cys
            100                 105                 110

His Cys Met Leu Phe Leu Thr Pro Asp Asn Asp Phe Ala Gly Lys Asp
        115                 120                 125

Gln Thr Ile Thr Ser Asp Glu Ile Lys Glu Thr Thr Ala His Met
    130                 135                 140

<210> SEQ ID NO 16
<211> LENGTH: 144
<212> TYPE: PRT
<213> ORGANISM: Glycine max
<220> FEATURE:
<221> NAME/KEY: misc_feature
<223> OTHER INFORMATION: CeresClone:470939

<400> SEQUENCE: 16
```

```
Met Thr Thr Gln Ala Ser Thr Phe Ala Val Ala Val Pro Ser Val Ala
1               5                   10                  15

Thr Pro Phe Arg Arg His Arg Asn Pro Phe Val Val Arg Ala Gln Ala
            20                  25                  30

Glu Pro Ser Asp Lys Ser Val Glu Ile Met Arg Lys Phe Ser Glu Gln
        35                  40                  45

Tyr Ala Arg Lys Ser Gly Thr Tyr Phe Cys Val Asp Lys Gly Val Thr
50                  55                  60

Ser Val Val Ile Lys Gly Leu Ala Asp His Lys Asp Thr Leu Gly Ala
65                  70                  75                  80

Pro Leu Cys Pro Cys Arg His Tyr Asp Asp Lys Ala Ala Glu Val Ala
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asn
            115                 120                 125

Glu Gln Thr Ile Thr Leu Asp Glu Ile Lys Glu Ser Thr Ala Asn Met
        130                 135                 140
```

<210> SEQ ID NO 17
<211> LENGTH: 148
<212> TYPE: PRT
<213> ORGANISM: Solanum tuberosum
<220> FEATURE:
<221> NAME/KEY: misc_feature
<223> OTHER INFORMATION: gi[14]275859

<400> SEQUENCE: 17

```
Met Arg Thr Leu Gln Ala Ser Thr Ser Tyr Ser Val Gly Phe Gly Ile
1               5                   10                  15

Ser Ser Phe Ala Thr Arg Pro Lys Pro Ser Thr His Arg Cys Leu Thr
            20                  25                  30

Val Ala Lys Met Glu Pro Ser Glu Lys Ser Val Glu Ile Met Arg Lys
        35                  40                  45

Phe Ser Glu Gln Tyr Ala Arg Arg Ser Glu Thr Tyr Phe Cys Met Asp
50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
            85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
            115                 120                 125

Phe Ala Gly Glu Glu Gln Thr Ile Ser Met Glu Glu Ile Lys Glu Thr
        130                 135                 140

Thr Ala Asn Met
145
```

<210> SEQ ID NO 18
<211> LENGTH: 152
<212> TYPE: PRT
<213> ORGANISM: Zea mays
<220> FEATURE:
<221> NAME/KEY: misc_feature
<223> OTHER INFORMATION: CeresClone:295783

<400> SEQUENCE: 18

-continued

```
Met Thr Ser Thr Val Thr Thr Val Gly Cys Gly Leu Pro Val
1               5                   10                  15

Arg Pro Leu Ser Thr Ala Thr Arg Gly Arg Pro Arg Cys Ala Val
            20                  25                  30

Arg Ala Gln Ala Ala Gly Ala Asp Ala Ser Asn Asp Lys Ser Val Glu
        35                  40                  45

Val Met Arg Lys Phe Ser Glu Gln Tyr Ala Arg Ser Asn Thr Phe
    50                  55                  60

Phe Cys Ala Asp Lys Thr Val Thr Ala Val Val Ile Lys Gly Leu Ala
65              70                  75                  80

Asp His Arg Asp Thr Leu Gly Ala Pro Leu Cys Pro Cys Arg His Tyr
                85                  90                  95

Asp Asp Lys Ala Ala Glu Val Ala Gln Gly Phe Trp Asn Cys Pro Cys
            100                 105                 110

Val Pro Met Arg Glu Arg Lys Glu Cys His Cys Met Leu Phe Leu Thr
            115                 120                 125

Pro Asp Asn Asp Phe Ala Gly Lys Asp Gln Val Ile Ser Phe Glu Glu
    130                 135                 140

Ile Lys Glu Ala Thr Ser Lys Phe
145                 150
```

<210> SEQ ID NO 19
<211> LENGTH: 146
<212> TYPE: PRT
<213> ORGANISM: Oryza sativa subsp. japonica
<220> FEATURE:
<221> NAME/KEY: misc_feature
<223> OTHER INFORMATION: gi[50]898984

<400> SEQUENCE: 19

```
Met Met Ser Met Ala Ser Thr Thr Ala Ser Pro Phe Cys Pro Ser Pro
1               5                   10                  15

Met Pro Arg Gly Arg Lys Cys Thr Val Arg Val Gln Ala Gly Ala Ala
            20                  25                  30

Gly Ala Asp Ala Ser Asp Lys Ser Leu Glu Ile Met Arg Lys Phe Ser
        35                  40                  45

Glu Gln Tyr Ala Arg Arg Ser Asn Thr Phe Phe Cys Ser Glu Lys Ser
    50                  55                  60

Val Thr Ala Val Val Ile Lys Gly Leu Ala Asp His Lys Asp Gln Leu
65              70                  75                  80

Gly Ala Pro Leu Cys Pro Cys Arg His Tyr Asp Asp Lys Ala Ala Glu
                85                  90                  95

Val Ala Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
            115                 120                 125

Gly Gln Asp Gln Ala Ile Thr Leu Glu Glu Ile Lys Asp Ala Thr Ser
    130                 135                 140

Lys Ile
145
```

<210> SEQ ID NO 20
<211> LENGTH: 1016
<212> TYPE: DNA
<213> ORGANISM: Arabidopsis thaliana
<220> FEATURE:
<221> NAME/KEY: misc_feature
<223> OTHER INFORMATION: clone126592_expected_L44

```
<400> SEQUENCE: 20
gttgaatcaa aaataatcag taacgctttg agtgaagatg atgaatgttg cagtgacagc      60
cactccctcg tctctcttgt actctcctct gcttcttcct tctcaagggc caaaccggcg     120
aatgcaatgg aaaagaaacg gaaagagacg gttagggaca aaggtggctg tttccggtgt     180
tatcacagct ggatttgagc tgaagccacc tccatatcct cttgatgctc tggaaccgca     240
tatgagccgg gaaaccttgg attatcactg gggcaaacat cacaaaactt atgtagagaa     300
cctgaacaag caaatcttag gcacggatct agatgcatta tccttggaag aagttgtgct     360
tctttcatac aacaaaggca atatgcttcc tgctttcaac aacgctgcac aggcttggaa     420
ccacgagttc ttctgggagt ctatccaacc tggaggtgga ggaaagccaa ctggagagct     480
cctcagatta atagaaagag attttgggtc tttcgaagag ttttttggaaa ggttcaagtc     540 ggctgcagct tcgaattttg gttcgggttg gacatggctt gcatataagg cgaatagact     600
tgacgttgca aatgccgtta atcctctccc aaaggaggaa gacaagaaac ttgttatagt     660
gaagacgccc aatgcagtaa atccgctcgt atgggattat tctccacttc tcaccattga     720
tacctgggag cacgcttact atctggattt tgagaaccga agagctgaat acataaatac     780
attcatggaa aagcttgtgt catgggaaac tgtaagcaca aggttggaat ccgcaattgc     840
tcgagcagtg caaagagaac aagaaggaac agagacagaa gatgaagaga tccagatga     900 tgaagtacca gaggtctatt tagatagtga catcgatgta tctgaggttg actaaaactt     960
gtgaagcaat aacattagca tcttaaatgt taattacaca gagcaaattt ttttgc       1016

<210> SEQ ID NO 21
<211> LENGTH: 305
<212> TYPE: PRT
<213> ORGANISM: Arabidopsis thaliana
<220> FEATURE:
<221> NAME/KEY: misc_feature
<223> OTHER INFORMATION: peptide_clone126592_expected_L44

<400> SEQUENCE: 21

Met Met Asn Val Ala Val Thr Ala Thr Pro Ser Ser Leu Leu Tyr Ser
 1               5                  10                  15

Pro Leu Leu Pro Ser Gln Gly Pro Asn Arg Arg Met Gln Trp Lys
             20                  25                  30

Arg Asn Gly Lys Arg Arg Leu Gly Thr Lys Val Ala Val Ser Gly Val
         35                  40                  45

Ile Thr Ala Gly Phe Glu Leu Lys Pro Pro Tyr Pro Leu Asp Ala
     50                  55                  60

Leu Glu Pro His Met Ser Arg Glu Thr Leu Asp Tyr His Trp Gly Lys
 65                  70                  75                  80

His His Lys Thr Tyr Val Glu Asn Leu Asn Lys Gln Ile Leu Gly Thr
                 85                  90                  95

Asp Leu Asp Ala Leu Ser Leu Glu Glu Val Val Leu Leu Ser Tyr Asn
                100                 105                 110

Lys Gly Asn Met Leu Pro Ala Phe Asn Asn Ala Ala Gln Ala Trp Asn
            115                 120                 125

His Glu Phe Phe Trp Glu Ser Ile Gln Pro Gly Gly Gly Gly Lys Pro
        130                 135                 140

Thr Gly Glu Leu Leu Arg Leu Ile Glu Arg Asp Phe Gly Ser Phe Glu
145                 150                 155                 160

Glu Phe Leu Glu Arg Phe Lys Ser Ala Ala Ala Ser Asn Phe Gly Ser
```

```
                    165                 170                 175
Gly Trp Thr Trp Leu Ala Tyr Lys Ala Asn Arg Leu Asp Val Ala Asn
                180                 185                 190
Ala Val Asn Pro Leu Pro Lys Glu Glu Asp Lys Lys Leu Val Ile Val
            195                 200                 205
Lys Thr Pro Asn Ala Val Asn Pro Leu Val Trp Asp Tyr Ser Pro Leu
        210                 215                 220
Leu Thr Ile Asp Thr Trp Glu His Ala Tyr Tyr Leu Asp Phe Glu Asn
225                 230                 235                 240
Arg Arg Ala Glu Tyr Ile Asn Thr Phe Met Glu Lys Leu Val Ser Trp
                245                 250                 255
Glu Thr Val Ser Thr Arg Leu Glu Ser Ala Ile Ala Arg Ala Val Gln
                260                 265                 270
Arg Glu Gln Glu Gly Thr Glu Thr Glu Asp Glu Asn Pro Asp Asp
            275                 280                 285
Glu Val Pro Glu Val Tyr Leu Asp Ser Asp Ile Asp Val Ser Glu Val
        290                 295                 300
Asp
305

<210> SEQ ID NO 22
<211> LENGTH: 1016
<212> TYPE: DNA
<213> ORGANISM: Arabidopsis thaliana
<220> FEATURE:
<221> NAME/KEY: misc_feature
<223> OTHER INFORMATION: clone126592_inplanta_experimental_L44

<400> SEQUENCE: 22
gttgaatcaa aaataatcag taacgctttg agtgaagatg atgaatgttg cagtgacagc      60
cactccctcg tctctcttgt actctcctct gcttcttcct tctcaagggc caaaccggcg    120
aatgcaatgg aaaagaaacg gaaagagacg gttagggaca aaggtggctg tttccggtgt    180
tatcacagct ggatttgagc tgaagccacc tccatatcct cttgatgctc tggaaccgca    240
tatgagccgg gaaaccttgg attatcactg gggcaaacat cacaaaactt atgtagagaa    300
cctgaacaag caaatcttag gcacggatct agatgcatta ccttggaag aagttgtgct     360
tctttcatac aacaaaggca atatgcttcc tgctttcaac aacgctgcac aggcttggaa    420
ccacgagttc ttctgggagt ctatccaacc tggaggtgga ggaaagccaa ctggagagct    480
cctcagatta atagaaagag attttgggtc tttcgaagag tttttggaaa ggttcaagtc    540
ggctgcagct tcgaattttg gttcgggttg gacatggctt gcatataagg cgaatagact    600
tgacgttgca aatgccgtta atcctctccc aaaggaggaa gacaagaaac ttgttatagt    660
gaagacgccc aatgcagtaa atccgctcgt atgggattat tctccacttc tcaccattga    720
tacctgggag cacgcttact atctggattt tgagaaccga agagctgaat acataaatac    780
attcatggaa aagcttgtgt catgggaaac tgtaagcaca aggttggaat ccgcaattgc    840
tcgagcagtg caaagagaac aagaaagaac agagacagaa gatgaagaga atccagatga    900
tgaagtacca gaggtctatt tagatagtga catcgatgta tctgaggttg actaaaactt    960
gtgaagcaat aacattagca tcttaaatgt taattacaca gagcaaattt ttttgc        1016

<210> SEQ ID NO 23
<211> LENGTH: 305
<212> TYPE: PRT
<213> ORGANISM: Arabidopsis thaliana
```

```
<220> FEATURE:
<221> NAME/KEY: misc_feature
<223> OTHER INFORMATION: peptide_clone126592_inplanta_experimental_L44

<400> SEQUENCE: 23
```

| | | | | | | | | | | | | | | | |
|---|---|---|---|---|---|---|---|---|---|---|---|---|---|---|---|
| Met | Met | Asn | Val | Ala | Val | Thr | Ala | Thr | Pro | Ser | Ser | Leu | Leu | Tyr | Ser |
| 1 | | | | 5 | | | | | 10 | | | | | 15 | |
| Pro | Leu | Leu | Leu | Pro | Ser | Gln | Gly | Pro | Asn | Arg | Arg | Met | Gln | Trp | Lys |
| | | | 20 | | | | | 25 | | | | | 30 | | |
| Arg | Asn | Gly | Lys | Arg | Arg | Leu | Gly | Thr | Lys | Val | Ala | Val | Ser | Gly | Val |
| | | 35 | | | | | 40 | | | | | 45 | | | |
| Ile | Thr | Ala | Gly | Phe | Glu | Leu | Lys | Pro | Pro | Tyr | Pro | Leu | Asp | Ala | |
| | 50 | | | | | 55 | | | | | 60 | | | | |
| Leu | Glu | Pro | His | Met | Ser | Arg | Glu | Thr | Leu | Asp | Tyr | His | Trp | Gly | Lys |
| 65 | | | | | 70 | | | | | 75 | | | | | 80 |
| His | His | Lys | Thr | Tyr | Val | Glu | Asn | Leu | Asn | Lys | Gln | Ile | Leu | Gly | Thr |
| | | | | 85 | | | | | 90 | | | | | 95 | |
| Asp | Leu | Asp | Ala | Leu | Ser | Leu | Glu | Glu | Val | Val | Leu | Leu | Ser | Tyr | Asn |
| | | | 100 | | | | | 105 | | | | | 110 | | |
| Lys | Gly | Asn | Met | Leu | Pro | Ala | Phe | Asn | Asn | Ala | Ala | Gln | Ala | Trp | Asn |
| | | 115 | | | | | 120 | | | | | 125 | | | |
| His | Glu | Phe | Phe | Trp | Glu | Ser | Ile | Gln | Pro | Gly | Gly | Gly | Lys | Pro | |
| | 130 | | | | | 135 | | | | | 140 | | | | |
| Thr | Gly | Glu | Leu | Leu | Arg | Leu | Ile | Glu | Arg | Asp | Phe | Gly | Ser | Phe | Glu |
| 145 | | | | | 150 | | | | | 155 | | | | | 160 |
| Glu | Phe | Leu | Glu | Arg | Phe | Lys | Ser | Ala | Ala | Ala | Ser | Asn | Phe | Gly | Ser |
| | | | | 165 | | | | | 170 | | | | | 175 | |
| Gly | Trp | Thr | Trp | Leu | Ala | Tyr | Lys | Ala | Asn | Arg | Leu | Asp | Val | Ala | Asn |
| | | | 180 | | | | | 185 | | | | | 190 | | |
| Ala | Val | Asn | Pro | Leu | Pro | Lys | Glu | Gly | Asp | Lys | Lys | Leu | Val | Ile | Val |
| | | 195 | | | | | 200 | | | | | 205 | | | |
| Lys | Thr | Pro | Asn | Ala | Val | Asn | Pro | Leu | Val | Trp | Asp | Tyr | Ser | Pro | Leu |
| | 210 | | | | | 215 | | | | | 220 | | | | |
| Leu | Thr | Ile | Asp | Thr | Trp | Glu | His | Ala | Tyr | Tyr | Leu | Asp | Phe | Glu | Asn |
| 225 | | | | | 230 | | | | | 235 | | | | | 240 |
| Arg | Arg | Ala | Glu | Tyr | Ile | Asn | Thr | Phe | Met | Glu | Lys | Leu | Val | Ser | Trp |
| | | | | 245 | | | | | 250 | | | | | 255 | |
| Glu | Thr | Val | Ser | Thr | Arg | Leu | Glu | Ser | Ala | Ile | Ala | Arg | Ala | Val | Gln |
| | | | 260 | | | | | 265 | | | | | 270 | | |
| Arg | Glu | Gln | Glu | Arg | Thr | Glu | Thr | Glu | Asp | Glu | Glu | Asn | Pro | Asp | Asp |
| | | 275 | | | | | 280 | | | | | 285 | | | |
| Glu | Val | Pro | Glu | Val | Tyr | Leu | Asp | Ser | Asp | Ile | Asp | Val | Ser | Glu | Val |
| | 290 | | | | | 295 | | | | | 300 | | | | |
| Asp | | | | | | | | | | | | | | | |
| 305 | | | | | | | | | | | | | | | |

```
<210> SEQ ID NO 24
<211> LENGTH: 158
<212> TYPE: PRT
<213> ORGANISM: Brassica napus
<220> FEATURE:
<221> NAME/KEY: misc_feature
<223> OTHER INFORMATION: CeresClone:970125

<400> SEQUENCE: 24
```

| | | | | | | | | | | | | | | | |
|---|---|---|---|---|---|---|---|---|---|---|---|---|---|---|---|
| Met | Met | Met | Thr | Thr | Thr | Ser | Ser | Leu | Leu | Ser | Pro | Cys | Ser | Leu | Leu |
| 1 | | | | 5 | | | | | 10 | | | | | 15 | |

```
Pro Ser Gln Gly Pro Asn Arg Gln Thr Gln Trp Lys Arg His Glu Lys
             20                  25                  30

Arg Gln Phe Ser Arg Lys Val Val Ser Gly Val Val Arg Ala Gly
         35                  40                  45

Phe Glu Leu Lys Pro Pro Tyr Pro Leu Asp Ala Leu Glu Pro His
 50                  55                  60

Met Ser Arg Glu Thr Met Asp Tyr His Trp Lys His His Arg Thr
 65                  70                  75                  80

Tyr Val Glu Asn Leu Asn Lys Gln Ile Leu Gly Thr Asp Leu Asp Gly
                 85                  90                  95

Leu Ser Leu Glu Glu Val Val Leu Leu Ser Tyr Asn Arg Gly Asn Met
            100                 105                 110

Leu Pro Val Phe Asn Asn Ala Ala Gln Ala Trp Asn His Glu Phe Phe
            115                 120                 125

Trp Glu Ser Ile Gln Pro Gly Gly Gly Lys Pro Ser Gly Asp Leu
    130                 135                 140

Leu Arg Leu Ile Glu Arg Asp Phe Gly Ser Phe Asp Asp Phe
145                 150                 155

<210> SEQ ID NO 25
<211> LENGTH: 313
<212> TYPE: PRT
<213> ORGANISM: Glycine max
<220> FEATURE:
<221> NAME/KEY: misc_feature
<223> OTHER INFORMATION: CeresClone:624535

<400> SEQUENCE: 25

Met Asn Leu Leu Ser Gln Ser Thr Ala Pro Ser Thr Ser Leu Ser Pro
 1               5                  10                  15

Ser Cys Phe Leu Pro Arg His Pro His Gly Ser Thr Trp Phe Ser Ser
             20                  25                  30

Gly Thr Phe Lys Phe Leu Lys Lys Glu Ser Arg Cys Leu Arg Lys Ala
         35                  40                  45

Gly Arg Thr Lys Ile Thr Ala Lys Phe Glu Leu Lys Pro Pro Tyr
 50                  55                  60

Pro Leu Ser Ala Leu Glu Pro Ile Met Ser Gln Glu Thr Leu Glu Tyr
 65                  70                  75                  80

His Trp Gly Lys His His Arg Thr Tyr Val Asp Asn Leu Asn Arg Gln
                 85                  90                  95

Ile Asp Gly Thr Asp Leu Asp Gly Asn Ser Leu Glu Asn Thr Ile Val
            100                 105                 110

Ile Thr Tyr Asn Lys Gly Asp Ile Leu Pro Ala Phe Asn Asn Ala Ala
            115                 120                 125

Gln Ala Trp Asn His Asp Phe Phe Trp Glu Ser Met Lys Pro Gly Gly
            130                 135                 140

Gly Gly Arg Pro Ser Gly Asp Leu Leu Asn Leu Ile Glu Arg Asp Phe
145                 150                 155                 160

Gly Ser Phe Glu Lys Phe Leu Asp Glu Phe Lys Thr Ala Ala Ser Thr
                165                 170                 175

Gln Phe Gly Ser Gly Trp Ala Trp Leu Ala Tyr Lys Glu Ser Arg Leu
            180                 185                 190

Asp Val Glu Asn Ala Val Asn Pro Leu Gln Ser Asp Glu Asp Lys Lys
            195                 200                 205

Leu Val Val Val Lys Thr Pro Asn Ala Val Asn Pro Leu Val Trp Asn
```

```
            210                 215                 220
Tyr Tyr His Pro Leu Leu Thr Ile Asp Val Trp Glu His Ala Tyr Phe
225                 230                 235                 240

Ile Asp Phe Gln Asn Gln Arg Arg Asp Tyr Ile Ser Val Phe Met Asp
                245                 250                 255

Lys Leu Val Ser Trp Asp Ala Val Ser Ser Arg Leu Glu Gln Ala Lys
                260                 265                 270

Ala Leu Ile Lys Glu Arg Glu Arg Glu Ala Glu Arg Lys Arg Arg Glu
                275                 280                 285

Glu Glu Glu Lys Arg Thr Ser Ser Glu Ala Ile Pro Glu Ile Tyr Ser
290                 295                 300

Asp Gly Asp Ala Asp Leu Asp Ala Glu
305                 310

<210> SEQ ID NO 26
<211> LENGTH: 313
<212> TYPE: PRT
<213> ORGANISM: Medicago sativa
<220> FEATURE:
<221> NAME/KEY: misc_feature
<223> OTHER INFORMATION: gi[16]974682

<400> SEQUENCE: 26

Met Lys Leu Leu Ser Pro Ser Ala Thr Ser Thr His Val Ser Ser
1               5                   10                  15

Ser Ala Phe Leu Pro Asn Val Ala Gly Phe Gln Asn Leu Gly Ser Ser
                20                  25                  30

Ser Val Thr Thr Phe Lys Phe Ser Lys Lys Gln Gly Arg Cys Ile Arg
                35                  40                  45

Arg Ala Gly Gly Thr Gln Ile Thr Ala Lys Phe Glu Leu Lys Pro Pro
50                  55                  60

Pro Tyr Pro Leu Asn Ala Ser Glu Pro Ile Met Ser Gln Asn Thr Phe
65                  70                  75                  80

Glu Tyr His Trp Gly Lys His Arg Ala Tyr Val Asp Asn Leu Asn
                85                  90                  95

Lys Gln Ile Glu Gly Thr Asp Leu Asp Gly Lys Ser Leu Glu Glu Thr
                100                 105                 110

Ile Ile Met Ser Tyr Asn Asn Gly Asp Ile Leu Pro Ala Phe Asn Asn
            115                 120                 125

Ala Ala Gln Val Trp Asn His Asp Phe Phe Trp Glu Ser Met Lys Pro
130                 135                 140

Gly Gly Gly Gly Lys Pro Ser Gly Glu Leu Leu Lys Leu Ile Glu Arg
145                 150                 155                 160

Asp Phe Gly Ser Phe Glu Lys Phe Val Glu Gln Phe Lys Leu Ala Ala
                165                 170                 175

Ser Thr Gln Phe Gly Ser Gly Trp Ala Trp Leu Ala Tyr Lys Glu Ser
                180                 185                 190

Arg Leu Asp Val Gly Asn Ala Val Asn Pro Leu Ala Thr Glu Glu Asp
                195                 200                 205

Lys Lys Leu Val Val Leu Lys Ser Pro Asn Ala Val Asn Pro Leu Val
                210                 215                 220

Trp Asn His His His Pro Leu Leu Thr Ile Asp Val Trp Glu His Ala
225                 230                 235                 240

Tyr Tyr Leu Asp Tyr Gln Asn Arg Arg Pro Glu Tyr Ile Ser Val Phe
                245                 250                 255
```

```
Met Asp Lys Leu Val Ser Trp Glu Ala Val Ser Ser Arg Leu Glu Lys
        260                 265                 270

Ala Lys Ala Val Ile Ala Glu Arg Glu Lys Glu Glu Arg Lys Arg
            275                 280                 285

Arg Glu Glu Glu Glu Lys Ser Thr Thr Gly Glu Asp Thr Pro Ala Pro
        290                 295                 300

Glu Ile Phe Ala Asp Ser Asp Thr Asp
305                 310
```

<210> SEQ ID NO 27
<211> LENGTH: 220
<212> TYPE: PRT
<213> ORGANISM: Zea mays
<220> FEATURE:
<221> NAME/KEY: misc_feature
<223> OTHER INFORMATION: CeresClone:278210

<400> SEQUENCE: 27

```
Met Ser Leu Gly Gln Met Met Leu Ala Ser Phe Asn Glu Gly Arg Glu
1               5                   10                  15

Gln Pro His Pro Pro Phe Phe His Ala Ala Gln Val Trp Asn His Asp
            20                  25                  30

Phe Tyr Trp Arg Ser Met Lys Pro Gly Gly Gly Gly Lys Pro Pro Glu
        35                  40                  45

Arg Leu Leu Lys Phe Ile Asn Arg Asp Phe Gly Ser Tyr Glu Gly Met
    50                  55                  60

Ile Arg Gln Phe Met Asp Ala Ala Leu Thr Gln Phe Gly Ser Gly Trp
65                  70                  75                  80

Val Trp Leu Ser Tyr Lys Gly Ser Gly Leu Pro Tyr Val Lys Ser Arg
                85                  90                  95

Ser Pro Ile Pro Ser Asp Asn His Gly Arg Leu Val Ile Ser Lys Thr
            100                 105                 110

Pro Asn Ala Ile Asn Pro Leu Val Trp Gly His Ser Pro Leu Leu Ala
        115                 120                 125

Ile Asp Val Trp Glu His Ala Tyr Tyr Leu Asp Tyr Glu Asp Arg Arg
    130                 135                 140

Ala Asp Tyr Val Ser Ala Ile Leu Glu Lys Leu Val Ser Trp Glu Thr
145                 150                 155                 160

Val Glu Ser Arg Leu Ala Lys Ala Val Ala Arg Ala Val Glu Arg Asp
                165                 170                 175

Glu His Leu Arg Arg Ile Leu Arg Lys Gln Arg Leu Ala Gln Ala
            180                 185                 190

Asn Gly Gln Ser Arg Ala Arg Ser Arg Ala Arg Gln Gly Arg Gln Gly
        195                 200                 205

Asp Gln Glu Val Ala Arg Ser Arg Pro Val Glu Ala
    210                 215                 220
```

<210> SEQ ID NO 28
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Promoter: 326; Report: 56

<400> SEQUENCE: 28

```
gtgggtaaaa gtatccttct ttgtgcattt ggtattttta agcatgtaat aagaaaaacc      60
aaaatagacg gctggtattt aataaaagga gactaatgta tgtatagtat atgatttgtg     120
```

```
tggaatataa taaagttgta aaatatagat gtgaagcgag tatctatctt ttgactttca    180
aaggtgatcg atcgtgttct tgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcattttg caggtaattt ctccttcgtt gctgctttgg cttgagcacg    780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaattttat cgcttggtgt    960
atttcgttat ttgcaaggcc ttggcccatt ttgagcccaa taactaaatc tagccttttc    1020
agaccggaca tgaacttcgc atattggcgt aactgtgcag ttttaccttt ttcggatcag    1080
acaagatcag atttgacca cccaacaata gtcagtcata tttgacaacc taagctagcc    1140
gacactacta aaaagcaaac aaaagaagaa ttctatgttg tcattttacc ggtggcaagt    1200
ggacccttct ataaaagagt aaagagacag cctgtgtgtg tataatctct aattatgttc    1260
accgacacaa tcacacaaac ccttctctaa tcacacaact tcttcatgat ttacgacatt    1320
aattatcatt aactctttaa attcacttta catgctcaaa aatatctaat ttgcagcatt    1380
aatttgagta ccgataacta ttattataat cgtcgtgatt cgcaatcttc ttcattagat    1440
gctgtcaagt tgtactcgca cgcggtggtc cagtgaagca aatccaacgg tttaaaacct    1500
tcttacattt ctagatctaa tctgaaccgt cagatatcta gatctcattg tctgaacaca    1560
gttagatgaa actgggaatg aatctggacg aaattacgat cttacaccaa cccctcgac    1620 gagctcgtat atataaagct tatacgctcc tccttcacct tcgtactact actaccacca    1680 catttctta gctcaaccta cattactaat ctccttttaa ggtatgttca cttttcttcg    1740
attcatactt tctcaagatt cctgcatttc tgtagaattt gaaccaagtg tcgattttg    1800 tttgagagaa gtgttgattt atagatctgg ttattgaatc tagattccaa ttttaattg    1860 attcgagttt gttatgtgtg tttatactac ttctcattga tcttgtttga tttctctgct    1920
ctgtattagg tttctttcgt gaatcagatc ggaa                                1954
```

<210> SEQ ID NO 29
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Promoter: 32449; Report: 92

<400> SEQUENCE: 29

```
gatcggcctt cttcaggtct tctctgtagc tctgttactt ctatcacagt tatcgggtat    60
ttgagaaaaa agagttagct aaaatgaatt ctccatata atcatggttt actacaggtt    120
tacttgattc gcgttagctt tatctgcatc caaagttttt tccatgatgt tatgtcatat    180
```

```
gtgataccgt tactatgttt ataactttat acagtctggt tcactggagt ttctgtgatt    240
atgttgagta catactcatt catcctttgg taactctcaa gtttaggttg tttgaattgc    300
ctctgttgtg atacttattg tctattgcat caatcttcta atgcaccacc ctagactatt    360
tgaacaaaga gctgtttcat cttaaacct ctgtgtctcc ttgctaaatg gtcatgcttt    420
aatgtcttca cctgtctttc tcttctatag atatgtagtc ttgctagata gttagttcta    480
cagctctctt ttgtagtctt gttagagagt tagttgagat attacctctt aaaagtatcc    540
ttgaacgctt tccggttatg accaatttgt tgtagctcct tgtaagtaga acttactggg    600
accagcgaga cagtttatgt gaatgttcat gcttaagtgt cgaacgtatc tatctctact    660
atagctctgt agtcttgtta dacagttagt tttatatctc cattttttg tagtcttgct    720 agttgagata ttacctcttc tcttcaaagt atccttgaac gctcaccggt tatgaaatct    780
ctacactata gctctgtagt cttgctagat agttagttct ttagctctct ttttgtagcc    840
tagttcttta gctctccttt tgtagccttg ctacagagta agatgggata ttacctcctt    900
gaacgctctc cggttatgac caatttgttg tagctccttg taagtagaac ttaggataga    960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta atttaccaa attctttatg   1260 aagtttaaat tatactcaca ttaaaaggat tattggataa tgtaaaaatt ctgaacaatt   1320
actgattttg gaaaattaac aaatattctt tgaaatagaa gaaaaagcct ttttcctttt   1380
gacaacaaca tataaaatca tactcccatt aaaaagattt taatgtaaaa ttctgaatat   1440
aagatatttt ttacaacaac aaccaaaaat atttatttt ttccttttt acagcaacaa   1500 gaaggaaaaa ctttttttt tgtcaagaaa aggggagatt atgtaaacag ataaaacagg   1560 gaaataact aaccgaactc tcttaattaa catcttcaaa taaggaaaat tatgatccgc   1620
atatttagga agatcaatgc attaaaacaa cttgcacgtg gaaagagaga ctatacgctc   1680
cacacaagtt gcactaatgg tacctctcac aaaccaatca aaatactgaa taatgccaac   1740
gtgtacaaat tagggtttta cctcacaacc atcgaacatt ctcgaaacat tttaaacagc   1800
ctggcgccat agatctaaac tctcatcgac caattttga ccgtccgatg gaaactctag   1860
cctcaaccca aaactctata taagaaatc ttttccttcg ttattgctta ccaaatacaa   1920
accctagccg ccttattcgt cttcttcgtt ctctagtttt ttcctcagtc tctgttctta   1980
gatcccttgt agtttccaaa tcttccgata aggcct                              2016
```

<210> SEQ ID NO 30
<211> LENGTH: 870
<212> TYPE: DNA
<213> ORGANISM: Arabidopsis thaliana
<220> FEATURE:
<221> NAME/KEY: misc_feature
<223> OTHER INFORMATION: Ceres cDNA 12333678

<400> SEQUENCE: 30

```
aaaaagtacg aaaggaaaat atgagtgagg agaagaggaa gcaacacttc gtgctagtac     60
atggtgcgtg ccacggcgca tggtgctggt acaaggttaa gctcttctc gaggctttgg    120 gccatcgtgt aaccgcctta gacctagctg cttccggtat agacacaacc aggtcaatca    180
```

```
ctgacatttc tacatgtgaa caatattctg agccattgat gcagctaatg acttcattgc    240
cgaatgatga gaaggttgta ctcgttggtc atagctttgg aggtttgagt ttagccttag    300
ccatggataa gtttcccgat aaaatctctg tctctgtctt cgtgactgca ttcatgcccg    360
acaccaaaca ctcaccatcg ttcgtcgagg aaaagtttgc aagcagcatg acaccagaag    420
gatggatggg ctctgagctc gagacatatg gttcagataa ttccggcttg tctgtgttct    480
tcagcaccga cttcatgaag caccgtctct accaactttc tcctgtggag gatcttgagc    540
ttggattgct tctaaagagg cctagttcat tgtttattaa tgaattatcg aagatggaga    600 actttctga gaagggtat ggatctgttc ctcgagctta cattgtgtgc aaagaggaca    660
acattatctc ggaagaccat caacgatgga tgatccataa ttatccggcg aatttagtga    720
ttgagatgga agagacggat catatgccaa tgttttgcaa acctcaagta ctaagtgacc    780
atctattggc aatcgctgac aatttctctt aaataatatt ttgatgaaaa tgtatttgga    840
gtggatacaa taaaaatgtg ttctaaatgg                                     870
```

<210> SEQ ID NO 31
<211> LENGTH: 263
<212> TYPE: PRT
<213> ORGANISM: Arabidopsis thaliana
<220> FEATURE:
<221> NAME/KEY: misc_feature
<223> OTHER INFORMATION: Peptide Ceres cDNA 12333678

<400> SEQUENCE: 31

```
Met Ser Glu Glu Lys Arg Lys Gln His Phe Val Leu Val His Gly Ala
1               5                   10                  15

Cys His Gly Ala Trp Cys Trp Tyr Lys Val Lys Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
    50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Phe Ala Ser
        115                 120                 125

Ser Met Thr Pro Glu Gly Trp Met Gly Ser Glu Leu Glu Thr Tyr Gly
    130                 135                 140

Ser Asp Asn Ser Gly Leu Ser Val Phe Phe Ser Thr Asp Phe Met Lys
145                 150                 155                 160

His Arg Leu Tyr Gln Leu Ser Pro Val Glu Asp Leu Glu Leu Gly Leu
                165                 170                 175

Leu Leu Lys Arg Pro Ser Ser Leu Phe Ile Asn Glu Leu Ser Lys Met
            180                 185                 190

Glu Asn Phe Ser Glu Lys Gly Tyr Gly Ser Val Pro Arg Ala Tyr Ile
        195                 200                 205

Val Cys Lys Glu Asp Asn Ile Ile Ser Glu Asp His Gln Arg Trp Met
    210                 215                 220

Ile His Asn Tyr Pro Ala Asn Leu Val Ile Glu Met Glu Glu Thr Asp
```

```
              225                 230                 235                 240

His Met Pro Met Phe Cys Lys Pro Gln Val Leu Ser Asp His Leu Leu
                245                 250                 255

Ala Ile Ala Asp Asn Phe Ser
            260

<210> SEQ ID NO 32
<211> LENGTH: 267
<212> TYPE: PRT
<213> ORGANISM: Citrus sinensis
<220> FEATURE:
<221> NAME/KEY: misc_feature
<223> OTHER INFORMATION: gi[14]279437

<400> SEQUENCE: 32

Met Glu Glu Val Val Gly Met Glu Glu Lys His Phe Val Leu Val His
1               5                   10                  15

Gly Val Asn His Gly Ala Trp Cys Trp Tyr Lys Leu Lys Ala Arg Leu
                20                  25                  30

Val Ala Gly Gly His Arg Val Thr Ala Val Asp Leu Ala Ala Ser Gly
            35                  40                  45

Ile Asn Met Lys Arg Ile Glu Asp Val His Thr Phe His Ala Tyr Ser
50                  55                  60

Glu Pro Leu Met Glu Val Leu Ala Ser Leu Pro Ala Glu Glu Lys Val
65                  70                  75                  80

Ile Leu Val Gly His Ser Leu Gly Gly Val Thr Leu Ala Leu Ala Gly
                85                  90                  95

Asp Lys Phe Pro His Lys Ile Ser Val Ala Val Phe Val Thr Ala Phe
                100                 105                 110

Met Pro Asp Thr Thr His Arg Pro Ser Phe Val Leu Glu Gln Tyr Ser
            115                 120                 125

Glu Lys Met Gly Lys Glu Asp Asp Ser Trp Leu Asp Thr Gln Phe Ser
130                 135                 140

Gln Cys Asp Ala Ser Asn Pro Ser His Ile Ser Met Leu Phe Gly Arg
145                 150                 155                 160

Glu Phe Leu Thr Ile Lys Ile Tyr Gln Leu Cys Pro Pro Glu Asp Leu
                165                 170                 175

Glu Leu Ala Lys Met Leu Val Arg Pro Gly Ser Met Phe Ile Asp Asn
            180                 185                 190

Leu Ser Lys Glu Ser Lys Phe Ser Asp Glu Gly Tyr Gly Ser Val Lys
        195                 200                 205

Arg Val Tyr Leu Val Cys Glu Glu Asp Ile Gly Leu Pro Lys Gln Phe
    210                 215                 220

Gln His Trp Met Ile Gln Asn Tyr Pro Val Asn Glu Val Met Glu Ile
225                 230                 235                 240

Lys Gly Gly Asp His Met Ala Met Leu Ser Asp Pro Gln Lys Leu Cys
                245                 250                 255

Asp Cys Leu Ser Gln Ile Ser Leu Lys Tyr Ala
            260                 265

<210> SEQ ID NO 33
<211> LENGTH: 263
<212> TYPE: PRT
<213> ORGANISM: Arabidopsis thaliana
<220> FEATURE:
<221> NAME/KEY: misc_feature
<223> OTHER INFORMATION: CeresClone:1010900
```

-continued

```
<400> SEQUENCE: 33

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65              70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 34
<211> LENGTH: 263
<212> TYPE: PRT
<213> ORGANISM: Arabidopsis thaliana
<220> FEATURE:
<221> NAME/KEY: misc_feature
<223> OTHER INFORMATION: gi[20]196998

<400> SEQUENCE: 34

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65              70                  75                  80
```

```
Leu Val Gly His Ser Phe Gly Leu Asn Leu Ala Ile Ala Met Glu
            85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
            115                 120                 125

Asn Met Pro Gln Glu Ala Trp Met Gly Thr Glu Phe Glu Pro Tyr Gly
130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
            195                 200                 205

Val Cys Lys Glu Asp Lys Ala Ile Pro Glu Glu Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 35
<211> LENGTH: 263
<212> TYPE: PRT
<213> ORGANISM: Arabidopsis thaliana
<220> FEATURE:
<221> NAME/KEY: misc_feature
<223> OTHER INFORMATION: gi[27]754457

<400> SEQUENCE: 35

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
            35                  40                  45

Thr Thr Arg Ser Ile Thr Asp Ile Pro Thr Cys Glu Gln Tyr Ser Glu
50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
            85                  90                  95

Lys Phe Pro Lys Lys Ile Ser Val Ala Val Phe Leu Thr Ala Phe Met
            100                 105                 110

Pro Asp Thr Glu His Ser Pro Ser Phe Val Leu Asp Lys Phe Gly Ser
            115                 120                 125

Asn Met Pro Gln Glu Ala Trp Met Gly Thr Glu Phe Glu Pro Tyr Gly
130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175
```

```
Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 36
<211> LENGTH: 257
<212> TYPE: PRT
<213> ORGANISM: Hevea brasiliensis
<220> FEATURE:
<221> NAME/KEY: misc_feature
<223> OTHER INFORMATION: gi[50]513520

<400> SEQUENCE: 36

Met Ala Phe Ala His Phe Val Leu Ile His Thr Ile Cys His Gly Ala
1               5                   10                  15

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
        115                 120                 125

Lys Asp Thr Thr Tyr Phe Thr Tyr Thr Lys Asp Gly Lys Glu Ile Thr
    130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
    210                 215                 220

Asp Lys Val Tyr Lys Val Glu Gly Gly Asp His Leu Leu Gln Leu Thr
225                 230                 235                 240

Lys Thr Lys Glu Ile Ala Glu Ile Leu Gln Glu Val Ala Asp Thr Tyr
                245                 250                 255

Asn
```

<210> SEQ ID NO 37
<211> LENGTH: 257
<212> TYPE: PRT
<213> ORGANISM: Hevea brasiliensis
<220> FEATURE:
<221> NAME/KEY: misc_feature
<223> OTHER INFORMATION: gi[64]35646

<400> SEQUENCE: 37

Met Ala Phe Ala His Phe Val Leu Ile His Thr Ile Cys His Gly Ala
1               5                   10                  15

Trp Ile Trp His Lys Leu Lys Pro Leu Glu Ala Leu Gly His Lys
            20                  25                  30

Val Thr Ala Leu Asp Leu Ala Ala Ser Gly Val Asp Pro Arg Gln Ile
            35                  40                  45

Glu Glu Ile Gly Ser Phe Asp Glu Tyr Ser Glu Pro Leu Leu Thr Phe
        50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
                100                 105                 110

Cys Pro Ser Tyr Val Val Asp Lys Leu Met Glu Val Phe Pro Asp Trp
            115                 120                 125

Lys Asp Thr Thr Tyr Phe Thr Tyr Thr Lys Asp Gly Lys Glu Ile Thr
130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
            195                 200                 205

Ile Phe Leu Pro Glu Phe Gln Leu Trp Gln Ile Glu Asn Tyr Lys Pro
        210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 38
<211> LENGTH: 258
<212> TYPE: PRT
<213> ORGANISM: Manihot esculenta
<220> FEATURE:
<221> NAME/KEY: misc_feature
<223> OTHER INFORMATION: gi[27]80225

<400> SEQUENCE: 38

Met Ala Val Val Asp Phe Val Leu Ile His Thr Ile Cys His Gly Ala
1               5                   10                  15

Trp Ile Trp Tyr Lys Leu Lys Pro Val Leu Glu Ala Ala Gly His Lys
            20                  25                  30

```
Val Thr Ala Leu Asp Leu Ala Ala Ser Gly Val Asp Pro Arg Gln Ile
         35                  40                  45

Glu Gln Ile Asn Ser Phe Asp Glu Tyr Ser Glu Pro Leu Leu Thr Phe
 50                  55                  60

Met Glu Ser Leu Pro Gln Gly Glu Lys Val Ile Leu Val Gly Glu Ser
 65                  70                  75                  80

Cys Gly Gly Leu Asn Ile Ala Ile Ala Ala Asp Lys Tyr Pro Glu Lys
                 85                  90                  95

Ile Ala Ala Ala Val Phe Gln Asn Ser Leu Leu Pro Asp Thr Lys His
                100                 105                 110

Lys Pro Ser Tyr Val Val Asp Lys Leu Met Glu Val Phe Pro Asp Trp
             115                 120                 125

Lys Asp Thr Glu Tyr Phe Glu Phe Ser Asn Ser Asn Gly Glu Thr Ile
130                 135                 140

Thr Gly Met Val Leu Gly Leu Lys Leu Met Arg Glu Asn Leu Tyr Thr
145                 150                 155                 160

Ile Cys Pro Pro Glu Asp Tyr Glu Leu Ala Lys Met Leu Thr Arg Arg
                165                 170                 175

Gly Ser Leu Phe Gln Ser Ile Leu Ala Gln Arg Glu Lys Phe Thr Glu
             180                 185                 190

Lys Gly Tyr Gly Ser Ile Lys Lys Ile Tyr Val Trp Thr Gly Asp Asp
         195                 200                 205

Lys Ile Phe Leu Pro Glu Phe Gln Leu Trp Gln Ile Glu Asn Tyr Lys
     210                 215                 220

Pro Asp Leu Val Phe Arg Val Met Gly Gly Asp His Lys Leu Gln Leu
225                 230                 235                 240

Thr Lys Thr Asn Glu Ile Ala Gly Ile Leu Gln Lys Val Ala Asp Ile
                245                 250                 255

Tyr Ala

<210> SEQ ID NO 39
<211> LENGTH: 258
<212> TYPE: PRT
<213> ORGANISM: Catharanthus roseus
<220> FEATURE:
<221> NAME/KEY: misc_feature
<223> OTHER INFORMATION: gi[53]830670

<400> SEQUENCE: 39

Met Glu Val Met Lys His Phe Val Thr Val His Gly Val Gly His Gly
 1               5                  10                  15

Ala Trp Val Tyr Tyr Lys Leu Lys Pro Arg Ile Glu Ala Ala Gly His
                 20                  25                  30

Arg Cys Thr Ala Val Asn Leu Ala Ala Ser Gly Ile Asn Glu Lys Lys
             35                  40                  45

Leu Glu Glu Val Arg Ser Ser Ile Asp Tyr Ala Ala Pro Leu Leu Glu
 50                  55                  60

Val Leu Asp Ser Val Pro Glu Asn Glu Lys Val Ile Leu Val Gly His
 65                  70                  75                  80

Ser Gly Gly Gly Met Thr Ala Ala Val Gly Met Glu Lys Phe Pro Asn
                 85                  90                  95

Lys Ile Ser Leu Ala Val Phe Leu Asn Ala Ile Met Pro Asp Thr Glu
                100                 105                 110

Asn Arg Pro Ser Tyr Val Leu Glu Glu Tyr Thr Ala Lys Thr Pro Pro
             115                 120                 125
```

-continued

```
Glu Ala Trp Lys Asp Cys Gln Phe Ser Ala Tyr Gly Asp Pro Pro Ile
    130                 135                 140

Thr Ser Leu Val Cys Gly Pro Glu Phe Ile Ser Ser Thr Leu Tyr His
145                 150                 155                 160

Leu Ser Pro Ile Glu Asp His Ala Leu Gly Lys Ile Leu Val Arg Pro
                165                 170                 175

Gly Ser Leu Phe Ile Glu Asp Leu Leu Lys Ala Glu Lys Phe Thr Glu
            180                 185                 190

Glu Gly Phe Gly Ser Val Pro Arg Val Tyr Val Ile Ala Ala Glu Asp
        195                 200                 205

Lys Thr Ile Pro Pro Glu Phe Gln Arg Trp Met Ile Glu Asn Asn Pro
    210                 215                 220

Val Lys Glu Val Lys Glu Ile Lys Gly Ala Asp His Met Pro Met Phe
225                 230                 235                 240

Ser Lys Pro Asp Glu Leu Ser Gln Cys Leu Leu Asp Ile Ala Lys Lys
                245                 250                 255

His Ala

<210> SEQ ID NO 40
<211> LENGTH: 264
<212> TYPE: PRT
<213> ORGANISM: Rauvolfia serpentina
<220> FEATURE:
<221> NAME/KEY: misc_feature
<223> OTHER INFORMATION: gi[66]51393

<400> SEQUENCE: 40

Met His Ser Ala Ala Asn Ala Lys Gln Gln Lys His Phe Val Leu Val
1               5                   10                  15

His Gly Gly Cys Leu Gly Ala Trp Ile Trp Tyr Lys Leu Lys Pro Leu
            20                  25                  30

Leu Glu Ser Ala Gly His Lys Val Thr Ala Val Asp Leu Ser Ala Ala
        35                  40                  45

Gly Ile Asn Pro Arg Arg Leu Asp Glu Ile His Thr Phe Arg Asp Tyr
    50                  55                  60

Ser Glu Pro Leu Met Glu Val Met Ala Ser Ile Pro Pro Asp Glu Lys
65                  70                  75                  80

Val Val Leu Leu Gly His Ser Phe Gly Gly Met Ser Leu Gly Leu Ala
                85                  90                  95

Met Glu Thr Tyr Pro Glu Lys Ile Ser Val Ala Val Phe Met Ser Ala
            100                 105                 110

Met Met Pro Asp Pro Asn His Ser Leu Thr Tyr Pro Phe Glu Lys Tyr
        115                 120                 125

Asn Glu Lys Cys Pro Ala Asp Met Met Leu Asp Ser Gln Phe Ser Thr
    130                 135                 140

Tyr Gly Asn Pro Glu Asn Pro Gly Met Ser Met Ile Leu Gly Pro Gln
145                 150                 155                 160

Phe Met Ala Leu Lys Met Phe Gln Asn Cys Ser Val Glu Asp Leu Glu
                165                 170                 175

Leu Ala Lys Met Leu Thr Arg Pro Gly Ser Leu Phe Phe Gln Asp Leu
            180                 185                 190

Ala Lys Ala Lys Lys Phe Ser Thr Glu Arg Tyr Gly Ser Val Lys Arg
        195                 200                 205

Ala Tyr Ile Phe Cys Asn Glu Asp Lys Ser Phe Pro Val Glu Phe Gln
    210                 215                 220
```

```
Lys Trp Phe Val Glu Ser Val Gly Ala Asp Lys Val Lys Glu Ile Lys
225                 230                 235                 240

Glu Ala Asp His Met Gly Met Leu Ser Gln Pro Arg Glu Val Cys Lys
                245                 250                 255

Cys Leu Leu Asp Ile Ser Asp Ser
            260

<210> SEQ ID NO 41
<211> LENGTH: 262
<212> TYPE: PRT
<213> ORGANISM: Lycopersicon esculentum
<220> FEATURE:
<221> NAME/KEY: misc_feature
<223> OTHER INFORMATION: gi[41]814856

<400> SEQUENCE: 41

Met Glu Lys Gly Asp Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45

Lys His Val Asp Asp Leu Asn Ser Met Ala Asp Tyr Asn Glu Pro Leu
    50                  55                  60

Met Glu Phe Met Asn Ser Leu Pro Gln Leu Glu Arg Val Val Leu Val
65                  70                  75                  80

Gly His Ser Met Gly Gly Ile Asn Ile Ser Leu Ala Met Glu Lys Phe
                85                  90                  95

Pro Gln Lys Ile Val Ala Val Phe Val Thr Ala Phe Met Pro Gly
            100                 105                 110

Pro Asp Leu Asn Leu Val Ala Leu Gly Gln Gln Tyr Asn Gln Gln Val
        115                 120                 125

Glu Ser His Met Asp Thr Glu Phe Val Tyr Asn Asn Gly Gln Asp Lys
    130                 135                 140

Ala Pro Thr Ser Leu Val Leu Gly Pro Glu Val Leu Ala Thr Asn Phe
145                 150                 155                 160

Tyr Gln Leu Ser Pro Pro Glu Asp Leu Thr Leu Ala Thr Tyr Leu Val
                165                 170                 175

Arg Pro Val Pro Leu Phe Asp Glu Ser Ile Leu Leu Ala Asn Thr Thr
            180                 185                 190

Leu Ser Lys Glu Lys Tyr Gly Ser Val His Arg Val Tyr Val Val Cys
        195                 200                 205

Asp Lys Asp Asn Val Leu Lys Glu Gln Gln Phe Gln Lys Trp Leu Ile
    210                 215                 220

Asn Asn Asn Pro Pro Asp Glu Val Gln Ile Ile His Asn Ala Asp His
225                 230                 235                 240

Met Val Met Phe Ser Lys Pro Arg Asp Leu Ser Ser Cys Leu Val Met
                245                 250                 255

Ile Ser Gln Lys Tyr Tyr
            260

<210> SEQ ID NO 42
<211> LENGTH: 260
<212> TYPE: PRT
<213> ORGANISM: Nicotiana tabacum
<220> FEATURE:
<221> NAME/KEY: misc_feature
<223> OTHER INFORMATION: gi[40]549303
```

<400> SEQUENCE: 42

Met Lys Glu Gly Lys His Phe Val Leu Val His Gly Ala Cys His Gly
1               5                   10                  15

Gly Trp Ser Trp Tyr Lys Leu Lys Pro Leu Leu Glu Ala Ala Gly His
            20                  25                  30

Lys Val Thr Ala Leu Asp Leu Ala Ala Ser Gly Thr Asp Leu Arg Lys
        35                  40                  45

Ile Glu Glu Leu Arg Thr Leu Tyr Asp Tyr Thr Leu Pro Leu Met Glu
50                  55                  60

Leu Met Glu Ser Leu Ser Ala Asp Glu Lys Val Ile Leu Val Gly His
65                  70                  75                  80

Ser Leu Gly Gly Met Asn Leu Gly Leu Ala Met Glu Lys Tyr Pro Gln
                85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
        115                 120                 125

Glu Asn Trp Leu Asp Thr Gln Phe Leu Pro Tyr Gly Ser Pro Glu Glu
130                 135                 140

Pro Leu Thr Ser Met Phe Phe Gly Pro Lys Phe Leu Ala His Lys Leu
145                 150                 155                 160

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260

<210> SEQ ID NO 43
<211> LENGTH: 262
<212> TYPE: PRT
<213> ORGANISM: Solanum tuberosum
<220> FEATURE:
<221> NAME/KEY: misc_feature
<223> OTHER INFORMATION: gi[56]392765

<400> SEQUENCE: 43

Met Glu Lys Gly Asn Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45

Lys His Val Glu Asp Leu Asn Ser Met Ala Asp Tyr Asn Glu Pro Leu
    50                  55                  60

Met Glu Phe Met Asn Ser Leu Pro Gln Gln Glu Arg Val Val Leu Val
65                  70                  75                  80

```
Gly His Ser Met Gly Gly Ile Asn Ile Ser Leu Ala Met Glu Lys Phe
                85                  90                  95

Pro His Lys Ile Ala Val Ala Val Phe Val Ser Ala Ser Met Pro Gly
            100                 105                 110

Pro Asp Leu Asn Leu Val Ala Val Thr Gln Gln Tyr Ser Gln Gln Val
            115                 120                 125

Glu Thr Pro Met Asp Thr Glu Phe Val Tyr Asn Asn Gly Leu Asp Lys
            130                 135                 140

Gly Pro Thr Ser Val Val Leu Gly Pro Lys Val Leu Ala Thr Ile Tyr
145                 150                 155                 160

Tyr Gln Phe Ser Pro Pro Glu Asp Leu Thr Leu Ala Thr Tyr Leu Val
                165                 170                 175

Arg Pro Val Pro Leu Phe Asp Glu Ser Val Leu Leu Thr Asn Thr Thr
            180                 185                 190

Leu Ser Lys Glu Lys Tyr Gly Ser Val His Arg Val Tyr Val Val Cys
            195                 200                 205

Asp Lys Asp Lys Val Leu Lys Glu Glu Gln Phe Gln Arg Trp Leu Ile
            210                 215                 220

Lys Asn Asn Pro Pro Asn Glu Val Gln Met Ile His Asp Ala Gly His
225                 230                 235                 240

Met Val Met Phe Ser Lys Pro Arg Glu Leu Cys Ser Cys Leu Val Met
                245                 250                 255

Ile Ser Gln Lys Tyr His
            260

<210> SEQ ID NO 44
<211> LENGTH: 266
<212> TYPE: PRT
<213> ORGANISM: Triticum aestivum
<220> FEATURE:
<221> NAME/KEY: misc_feature
<223> OTHER INFORMATION: CeresClone:644331

<400> SEQUENCE: 44

Met Glu Ala Cys Ala Gly Gln Ala Ser Ser Ala His Ile Val Leu Val
1               5                   10                  15

His Gly Ala Cys Leu Gly Gly Trp Ser Trp Phe Lys Val Ala Thr Arg
            20                  25                  30

Leu Arg Ser Ala Gly His Arg Val Ser Thr Pro Asp Leu Ala Ala Ser
            35                  40                  45

Gly Val Asp Pro Arg Pro Leu Arg Glu Val Pro Thr Phe Arg Asp Tyr
        50                  55                  60

Thr Lys Pro Leu Leu Asp Leu Leu Glu Ser Leu Pro Ser Gly Glu Lys
65                  70                  75                  80

Val Val Leu Val Gly His Ser Leu Gly Gly Val Asn Val Ala Leu Ala
                85                  90                  95

Cys Glu Leu Phe Pro Glu Lys Ile Ala Ala Ala Val Phe Val Ala Ala
            100                 105                 110

Phe Met Pro Asp His Arg Ser Pro Ser Tyr Val Leu Glu Lys Phe
            115                 120                 125

Val Glu Gly Arg Thr Leu Asp Trp Met Asp Thr Glu Phe Lys Pro Gln
            130                 135                 140

Asp Pro Glu Gly Lys Leu Pro Thr Ser Met Leu Phe Gly Pro Leu Val
145                 150                 155                 160

Thr Arg Ala Lys Phe Phe Gln Leu Cys Ser Pro Glu Asp Leu Thr Leu
```

-continued

```
                       165                 170                 175

Gly Arg Ser Leu Met Arg Val Asn Ser Met Phe Val Asp Asp Leu Arg
            180                 185                 190

Leu Gln Pro Pro His Thr Glu Ala Arg Tyr Gly Ser Val Arg Lys Ala
            195                 200                 205

Tyr Val Val Phe Lys Asp Asp His Ala Ile Val Glu Gln Phe Gln Arg
210                 215                 220

Trp Met Val His Asn Tyr Pro Val Asp Glu Val Met Glu Ile Asp Gly
225                 230                 235                 240

Ala Asp His Met Ala Leu Leu Ser Thr Pro Thr Glu Leu Ala Arg Cys
            245                 250                 255

Leu Ala Asp Ile Ala Val Lys Tyr Ala Ala
            260                 265

<210> SEQ ID NO 45
<211> LENGTH: 265
<212> TYPE: PRT
<213> ORGANISM: Triticum aestivum
<220> FEATURE:
<221> NAME/KEY: misc_feature
<223> OTHER INFORMATION: CeresClone:936068

<400> SEQUENCE: 45

Met Glu Gly Ser Ser Gly Lys His Phe Ile Leu Ile His Gly Leu
1               5                   10                  15

Cys His Gly Ala Trp Cys Trp Tyr Lys Leu Val Pro Met Leu Arg Ala
            20                  25                  30

Ala Gly His Arg Val Thr Ala Leu Asp Met Ala Ala Ser Gly Ala His
            35                  40                  45

Pro Ala Arg Met Asp Glu Val Pro Ser Phe Glu Asp Tyr Ser Trp Pro
50                  55                  60

Leu Leu Asp Ala Val Ala Ala Pro Ala Gly Glu Arg Leu Val Leu
65                  70                  75                  80

Val Gly His Ser Leu Gly Gly Leu Asn Ile Ala Leu Ala Met Glu Arg
            85                  90                  95

Phe Pro Arg Lys Val Ala Ala Val Phe Leu Ala Ala Cys Met Pro
            100                 105                 110

Cys Val Gly Arg His Met Gly Ala Thr Thr Glu Glu Ile Met Arg Arg
            115                 120                 125

Ile Lys Pro Asp Phe Phe Met Asp Met Lys Arg Met Val Leu Asn Thr
130                 135                 140

Ser Gln Gly Pro Arg Pro Ala Leu Val Phe Gly Pro Lys Ile Leu Ala
145                 150                 155                 160

Ala Lys Leu Tyr Asp Arg Ser Ser Gly Glu Asp Gln Thr Leu Ala Thr
            165                 170                 175

Met Leu Val Arg Pro Gly Cys Gln Phe Leu Asp Asp Pro Thr Met Lys
            180                 185                 190

Asp Glu Ala Leu Leu Thr Glu Ala Lys Tyr Gly Ser Val Lys Lys Val
            195                 200                 205

Tyr Val Val Ala Met Ala Asp Ala Ser Asn Ser Glu Glu Met Gln Arg
210                 215                 220

Trp Met Val Asp Met Ser Pro Gly Thr Glu Ala Glu Ile Ala Gly
225                 230                 235                 240

Ala Asp His Met Ala Met Cys Ser Lys Pro Arg Glu Leu Cys Asp Val
            245                 250                 255
```

Leu Leu Arg Ile Ala Asp Lys Tyr Glu
            260             265

<210> SEQ ID NO 46
<211> LENGTH: 268
<212> TYPE: PRT
<213> ORGANISM: Oryza sativa subsp. japonica
<220> FEATURE:
<221> NAME/KEY: misc_feature
<223> OTHER INFORMATION: gi[34]907176

<400> SEQUENCE: 46

Met Glu Ile Ser Ser Ser Lys Lys His Phe Ile Leu Val His Gly
1               5                   10                  15

Leu Cys His Gly Ala Trp Cys Trp Tyr Arg Val Val Ala Ala Leu Arg
                20                  25                  30

Ala Ala Gly His Arg Ala Thr Ala Leu Asp Met Ala Ala Ser Gly Ala
            35                  40                  45

His Pro Ala Arg Val Asp Glu Val Gly Thr Phe Glu Glu Tyr Ser Arg
        50                  55                  60

Pro Leu Leu Asp Ala Val Ala Ala Ala Ala Pro Gly Glu Arg Leu
65                  70                  75                  80

Val Leu Val Gly His Ser His Gly Gly Leu Ser Val Ala Leu Ala Met
                85                  90                  95

Glu Arg Phe Pro Asp Lys Val Ala Ala Val Phe Val Ala Ala Ala
                100                 105                 110

Met Pro Cys Val Gly Lys His Met Gly Val Pro Thr Glu Glu Phe Met
            115                 120                 125

Arg Arg Thr Ala Pro Glu Gly Leu Leu Met Asp Cys Glu Met Val Ala
        130                 135                 140

Ile Asn Asn Ser Gln Gly Ser Gly Val Ala Ile Asn Leu Gly Pro Thr
145                 150                 155                 160

Phe Leu Ala Gln Lys Tyr Tyr Gln Gln Ser Pro Ala Glu Asp Leu Ala
                165                 170                 175

Leu Ala Lys Met Leu Val Arg Pro Gly Asn Gln Phe Met Asp Asp Pro
            180                 185                 190

Val Met Lys Asp Glu Ser Leu Leu Thr Asn Gly Asn Tyr Gly Ser Val
        195                 200                 205

Lys Lys Val Tyr Val Ile Ala Lys Ala Asp Ser Ser Thr Glu Glu
    210                 215                 220

Met Gln Arg Trp Met Val Ala Met Ser Pro Gly Thr Asp Val Glu Glu
225                 230                 235                 240

Ile Ala Gly Ala Asp His Ala Val Met Asn Ser Lys Pro Arg Glu Leu
                245                 250                 255

Cys Asp Ile Leu Ile Lys Ile Ala Asn Lys Tyr Glu
            260                 265

<210> SEQ ID NO 47
<211> LENGTH: 262
<212> TYPE: PRT
<213> ORGANISM: Oryza sativa (japonica cultivar-group)
<220> FEATURE:
<221> NAME/KEY: misc_feature
<223> OTHER INFORMATION: gi[57]899620

<400> SEQUENCE: 47

Met Glu Gly Ser Ser Ser Ser Lys His Phe Ile Leu Val His Gly
1               5                   10                  15

```
Leu Cys His Gly Ala Trp Cys Trp Tyr Lys Val Val Thr Met Leu Arg
            20                  25                  30

Ser Glu Gly His Arg Val Thr Ala Leu Asp Leu Ala Ala Ser Gly Val
        35                  40                  45

His Pro Ala Arg Val Asp Glu Val His Ser Phe Glu Glu Tyr Ser Gln
    50                  55                  60

Pro Leu Leu Asp Ala Val Ala Glu Ala Pro Gly Glu Arg Leu Ile
65                  70                  75                  80

Leu Val Gly His Ser Phe Gly Gly Leu Ser Ile Ala Leu Ala Met Glu
                85                  90                  95

Arg Phe Pro Glu Lys Ile Ala Val Ala Val Phe Val Ala Ala Ala Val
            100                 105                 110

Pro Cys Val Gly Lys Arg Ile Ile Pro Glu Leu Ile Arg Glu Lys Ala
            115                 120                 125

Pro Lys Asp Met Leu Leu Asp Ser Lys Met Ile Pro Ile Asn Asn Lys
    130                 135                 140

Gln Gly Pro Gly Thr Ala Ile Leu Leu Gly Pro Asn Phe Leu Ala Glu
145                 150                 155                 160

Lys Gly Tyr Pro Leu Ser Pro Ala Glu Asp Leu Thr Leu Ala Lys Leu
                165                 170                 175

Leu Val Arg Pro Thr Ser Gln Phe Val Asp Asp Pro Thr Met Lys Asp
            180                 185                 190

Asp Arg Leu Leu Thr Ser Ala Asn Tyr Gly Ser Val Lys Arg Val Cys
        195                 200                 205

Leu Met Ala Met Glu Asp Asp Leu Lys Glu Val His Arg Tyr Met Ile
    210                 215                 220

Thr Leu Ser Pro Gly Val Glu Val Glu Glu Ile Ala Gly Ala Asp His
225                 230                 235                 240

Ala Val Met Cys Ser Arg Pro Arg Glu Leu Ser Asp Leu Leu Ala Lys
                245                 250                 255

Ile Gly Ser Lys Tyr Asp
            260

<210> SEQ ID NO 48
<211> LENGTH: 265
<212> TYPE: PRT
<213> ORGANISM: Capsella rubella
<220> FEATURE:
<221> NAME/KEY: misc_feature
<223> OTHER INFORMATION: gi[15]866583

<400> SEQUENCE: 48

Met Gly Gly Asp Gly Gly Ala Glu Gln Pro Val Ile His Phe Val Phe
1               5                   10                  15

Val His Gly Ala Ser His Gly Ala Trp Cys Trp Tyr Lys Leu Thr Ser
            20                  25                  30

Leu Leu Glu Thr Ala Gly Phe Lys Thr Thr Ser Val Asp Leu Thr Gly
        35                  40                  45

Ala Gly Ile Ser Val Thr Asp Ser Asn Thr Val Leu Glu Ser Asp Gln
    50                  55                  60

Tyr Asn Arg Pro Leu Phe Ser Leu Leu Ser Asp Leu Pro Pro Ser His
65                  70                  75                  80

Lys Val Ile Leu Val Gly His Ser Ile Gly Gly Ser Val Thr Asp
                85                  90                  95

Ala Leu Cys Arg Phe Thr Asp Lys Ile Ser Met Ala Ile Tyr Leu Ala
            100                 105                 110
```

```
Ala Ser Met Val Lys Pro Gly Ser Val Pro Pro His Val Ser Asp
        115                 120                 125

Met His Ala Asp Ala Arg Glu Glu Asn Ile Trp Glu Tyr Thr Tyr Gly
130                 135                 140

Glu Gly Thr Asp Lys Pro Pro Thr Gly Val Ile Met Lys Gln Glu Phe
145                 150                 155                 160

Leu Arg Gln Tyr Tyr Ser Gln Ser Pro Leu Glu Asp Val Ser Leu
        165                 170                 175

Ala Thr Lys Leu Leu Arg Pro Ala Pro Met Arg Ala Phe Gln Asp Leu
        180                 185                 190

Asp Lys Ser Pro Pro Asn Pro Glu Val Glu Lys Val Pro Arg Val Tyr
        195                 200                 205

Ile Lys Thr Gly Lys Asp Asn Leu Phe Ser Ser Val Arg Gln Asp Leu
        210                 215                 220

Leu Val Lys Asn Trp Pro Pro Ser Gln Phe Tyr Val Leu Glu Ser
225                 230                 235                 240

Asp His Ser Ala Phe Phe Ser Val Pro Thr Thr Leu Phe Val Tyr Leu
        245                 250                 255

Leu Arg Ala Val Ser Phe Leu His Lys
        260                 265
```

```
<210> SEQ ID NO 49
<211> LENGTH: 265
<212> TYPE: PRT
<213> ORGANISM: Lycopersicon hirsutum f. glabratum
<220> FEATURE:
<221> NAME/KEY: misc_feature
<223> OTHER INFORMATION: gi[56]393011
<220> FEATURE:
<221> NAME/KEY: misc_feature
<222> LOCATION: (46)..(46)
<223> OTHER INFORMATION: Xaa can be any naturally occurring amino acid

<400> SEQUENCE: 49
```

```
Met Glu Lys Ser Met Ser Pro Phe Val Lys His Phe Val Leu Val
1               5                   10                  15

His Thr Ala Phe His Gly Ala Trp Cys Trp Tyr Lys Ile Val Ala Leu
            20                  25                  30

Met Arg Ser Ser Gly His Asn Val Thr Ala Leu Asp Leu Xaa Ala Ser
        35                  40                  45

Gly Ile Asn Pro Lys Gln Ala Leu Gln Ile Pro Asn Phe Ser Asp Tyr
    50                  55                  60

Leu Ser Pro Leu Met Glu Phe Met Ala Ser Leu Pro Ala Asn Glu Lys
65                  70                  75                  80

Ile Ile Leu Val Gly His Ala Leu Gly Gly Leu Ala Ile Ser Lys Ala
            85                  90                  95

Met Glu Thr Phe Pro Glu Lys Ile Ser Val Ala Val Phe Leu Ser Gly
                100                 105                 110

Leu Met Pro Gly Pro Asn Ile Asp Ala Thr Thr Val Cys Thr Lys Ala
        115                 120                 125

Gly Ser Ala Val Leu Gly Gln Leu Asp Asn Cys Val Thr Tyr Glu Asn
    130                 135                 140

Gly Pro Thr Asn Pro Pro Thr Thr Leu Ile Ala Gly Pro Lys Phe Leu
145                 150                 155                 160

Ala Thr Asn Val Tyr His Leu Ser Pro Ile Glu Asp Leu Ala Leu Ala
            165                 170                 175
```

```
                                        -continued
Thr Ala Leu Val Arg Pro Leu Tyr Leu Tyr Leu Ala Glu Asp Ile Ser
            180             185             190

Lys Glu Val Val Leu Ser Ser Lys Arg Tyr Gly Ser Val Lys Arg Val
        195             200             205

Phe Ile Val Ala Thr Glu Asn Asp Ala Leu Lys Lys Glu Phe Leu Lys
    210             215             220

Leu Met Ile Glu Lys Asn Pro Pro Asp Glu Val Lys Glu Ile Glu Gly
225             230             235             240

Ser Asp His Val Thr Met Met Ser Lys Pro Gln Gln Leu Phe Thr Thr
            245             250             255

Leu Leu Ser Ile Ala Asn Lys Tyr Lys
            260             265
```

NUCLEOTIDE SEQUENCES AND POLYPEPTIDES ENCODED THEREBY USEFUL FOR MODIFYING PLANT CHARACTERISTICS

This Nonprovisional application claims priority under 35 U.S.C. § 119(e) on U.S. Provisional Application No. 60/575,309 filed on May 27, 2004, the entire contents of which are hereby incorporated by reference.

FIELD OF THE INVENTION

The present invention relates to isolated polynucleotides, polypeptides encoded thereby, and the use of those sequences for making transgenic plants with modulated pH response and phosphate use efficiency.

BACKGROUND OF THE INVENTION

Plants are constantly exposed to a variety of biotic (i.e., pathogen infection and insect herbivory) and abiotic (e.g., high pH, low phosphate) stresses. To survive these challenges, plants have developed elaborate mechanisms to perceive external signals and environmental stresses and to manifest adaptive responses with proper physiological and morphological changes (Bohnert et al., 1995). Plants exposed to low or high pH conditions typically have low yields of plant material, seeds, fruit and other edible products. Extreme soil pH conditions have a major influence on nutrient availability resulting in severe agronomic losses. Plants exposed to low pH soil conditions develop deficiencies in nutrients such as copper, molybdate, potassium, sulfur, and nitrogen. Also, plants exposed to high pH soil conditions develop iron, copper, manganese, and zinc deficiencies (FIG. 1). Phosphate deficiency is a problem in both high and low pH soil conditions. Essential mineral nutrients are required in substantial amounts to sustain plant growth and maximize plant yields.

Consequently, agricultural and horticultural entities routinely alter the rhizosphere to maximize and maintain crop yields; these frequently result in more pollution and unbalancing of the natural soil mineral balance (National Research Council. (1989) Alternative Agriculture. National Academic Press, Washington D.C.). Excessive over-liming of acid soils, for instance, has resulted in the induction of iron, manganese, copper, and zinc deficiencies; deficiencies commonly observed in calcareous soil.

It would, therefore, be of great interest and importance to be able to identify genes that confer improved phosphate efficiency characteristics to thereby enable one to create transformed plants (such as crop plants) with improved phosphate efficiency characteristics to thereby better survive low and high pH conditions.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. (Zhang et al. (2004) *Plant Physiol.* 135:615). There is a need for generally applicable processes that improve forest or agricultural plant growth potential. Therefore, the present invention relates to a process for increasing the abiotic stress tolerance and consequently the growth potential in plants, characterized by expression of recombinant DNA molecules stably integrated into the plant genome.

SUMMARY OF THE INVENTION

The present invention, therefore, relates to isolated polynucleotides, polypeptides encoded thereby, and the use of those sequences for making transgenic plants with modulated pH tolerance or phosphate use efficiency.

The present invention also relates to processes for increasing the growth potential in plants under abnormal pH or phosphate conditions, recombinant nucleic acid molecules and polypeptides used for these processes and their uses, as well as to plants themselves.

Unless otherwise defined, all technical and scientific terms used herein have the same meaning as commonly understood by one of ordinary skill in the art to which this invention belongs.

BRIEF DESCRIPTION OF THE FIGURES

FIG. 1 shows the relationship between soil pH and nutrient uptake.

FIG. 2 shows pH recovery as measured by volume of seeds collected from a plant containing cDNA 1248777 compared to pH treated and un-treated controls.

DETAILED DESCRIPTION OF THE INVENTION

1. Definitions

The following terms are utilized throughout this application:

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical and within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily to the same degree. Typically, comparable proteins give the same characteristics where the quantitative measurement due to one of the comparables is at lest 20% of the other; more typically, between 30 to 40%; even more typically, between 50-60%; even more typically, 70 to 80%; even more typically between 90 to 100%.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High pH: "High pH" can be defined as a non-optimal and terminal alkaline pH value when a given plant can no longer make use of certain essential nutrients, such as phosphate, available in the soil. For instance, if a plant grows optimally at pH of 4.0-5.0, high pH would be any pH greater than 5. If the optimal pH were in the range of 6-6.5, high pH would be a pH greater than pH 6.5. As an example, if a corn crop under optimal pH conditions would yield 134 bushels per acre and all other conditions were held constant, a high pH tolerant variety would produce similar yields at pH 9 or above.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Low Nitrogen: "Low nitrogen" can be defined as a quantity of nitrogen, whether in the form of ammonium or nitrate, which is insufficient to sustain normal growth and yield for a given plant. The need for nitrogen fertilizers varies considerably among plants. Further, the type of soil and the conditions in the soil have a significant impact on the ability of a plant to take up nitrogen. Supplemental nitrogen fertilizers are often added to soil or applied directly to plants to enhance their growth or appearance. Even with normal fertilizer applications, the amount of nitrogen available to a plant at any given time may be too low to support optimal growth. Hence, low nitrogen must be defined in terms of the specific plant and environment in which the plant is being grown. For example, if under a given set of conditions with a specific corn hybrid the optimal nitrogen level was 160 pounds of nitrogen fertilizer per acre and under such conditions the hybrid were able to achieve a yield of 134 bushels per acre, a low nitrogen tolerant hybrid would grow optimally and produce the same yield with at least 10% less or at least 20% less or at least 30% less or at least 40% less or at least 50% less nitrogen. Further, the low nitrogen hybrid would grow better after much of the initial nitrogen had been depleted and would not require multiple applications of nitrogen.

Low pH: "Low pH" can be defined as that non-optimal and terminal acidic pH value when a given plant can no longer make use of certain essential nutrients, such as potassium, available in the soil. If a plant grows optimally at pH of 4.0-5.0, low pH is any pH less than 4. If the optimal pH is in the range of 6-8, low pH would be a pH less than 6. For example, if a corn crop under optimal pH conditions would yield 134 bushels per acre and all other conditions were held constant, a low pH tolerant variety would produce similar yields at pH 5, or pH 4.

Low Phosphate: "Low phosphate" can be defined as a quantity of phosphate which is insufficient to sustain normal growth and yield for a given plant. The level of phosphate required for optimal plant growth differs among plant species and depends on the condition of the soil and other environmental conditions. To determine a level of phosphate that is low, comparative experiments are needed. For example, if a corn hybrid in a particular field treated with 40 pounds of phosphate per acre would yield 134 bushels per acre and all other conditions were held constant, a low phosphate tolerant hybrid would produce similar yields at 35 or less pounds of phosphate per acre or 30 or less pounds of phosphate per acre or 25 or less pounds of phosphate per acre or 20 or less pounds of phosphate per acre.

Masterpool: The "master pools" discussed in these experiments are a pool of seeds from five different transgenic plants transformed with the same exogenous gene.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30(2):321-9.); RCc2 and RCc3, promoters that direct root-specific gene transcription in rice (Xu et al., *Plant Mol. Biol.* 27:237 (1995) and TobRB27, a root-specific promoter from tobacco (Yamamoto et al., *Plant Cell* 3:371 (1991)).

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\% \ G+C) - 500/L \ 0.63(\% \ \text{formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools". Thus, the superpool contains an equal amount of seed from 500 different events, but only represents 100 transgenic plants with a distinct exogenous nucleotide sequence transformed into them, because the master pools are of 5 different events with the same exogenous nucleotide sequence transformed into them.

$T_0$: As used in the current application, the term "$T_0$" refers to the whole plant, explant, or callous tissue inoculated with the transformation medium.

$T_1$: As used in the current application, the term $T_1$ refers to the either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Zero Nitrogen: Nitrogen is not present in any amount.

Zero Phosphorus: Phosphorus is not present in any amount.

2. Important Characteristics of the Polynucleotides and Polypeptides of the Invention The polynucleotides and polypeptides of the present invention are of interest because when they are misexpressed (i.e. when expressed at a non-natural location or in an increased or decreased amount) they produce plants with modified pH tolerance or phosphate use efficiency. "Phosphate use efficiency" is a term that includes various responses to environmental conditions that affect the amount of phosphate available to the plant. For example, under both low and high pH conditions phosphate is bound within the soil, resulting in a decrease of available phosphate for maintaining or initiating physiological processes. As used herein, modulating phosphate use efficiency is intended to encompass all of these situations as well as other environmental situations that affect the plant's ability to use and/or maintain phosphate effectively (e.g. osmotic stress, etc.).

The polynucleotides and polypeptides of the invention, as discussed below and as evidenced by the results of various experiments, are useful for modulating pH tolerance or phosphate use efficiency. These traits can be used to exploit or maximize plant products for agricultural, ornamental or forestry purposes in different environment conditions of water supply. Modulating the expression of the nucleotides and polypeptides of the present invention leads to transgenic plants that will be less sensitive to variations in pH and that require less phosphate, resulting in better yields under these types of adverse conditions. Both categories of transgenic plants lead to reduced costs for the farmer and better yield in their respective environmental conditions.

3. The Polynucleotides and Polypeptides of the Invention

The polynucleotides of the invention, and the proteins expressed thereby, are set forth in the sequences present in the Sequence Listing. Some of these sequences are functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity and generally share at least one biochemical and/or phenotypic activity. For example, biochemical functionally comparable proteins are proteins that act on the same reactant to give the same product.

Another class of functionally comparable proteins is phenotypic functionally comparable proteins. The members of this class regulate the same physical characteristic, such as increased drought tolerance. Proteins can be considered phenotypic functionally comparable proteins even if the proteins give rise to the same physical characteristic, but to a different degree.

The polypeptides of the invention also include those comprising the consensus sequences described in Tables 1-5, 2-6 and 3-5. A consensus sequence defines the important conserved amino acids and/or domains within a polypeptide. Thus, all those sequences that conform to the consensus sequence are suitable for the same purpose. Polypeptides comprised of a sequence within and defined by one of the consensus sequences can be utilized for the purposes of the invention namely to make transgenic plants with improved tolerance to heat or high or low water conditions.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);

(b) YAC: Burke et al., Science 236:806-812 (1987);

(c) PAC: Sternberg N. et al., Proc Natl Acad Sci USA. Jan; 87(1):103-7 (1990);

(d) Bacteria-Yeast Shuttle Vectors: Bradshaw et al., Nucl Acids Res 23: 4850-4856 (1995);

(e) Lambda Phage Vectors: Replacement Vector, e.g., Frischauf et al., J. Mol. Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors: Walden et al., Mol Cell Biol 1: 175-194 (1990); and (g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as p326 or CaMV35S. Alternatively, the plant promoter directs transcription of a sequence of the invention in a specific tissue manner (tissue-specific promoter) or is otherwise under more precise environmental control (inducible promoter). Various plant promoters, including constitutive, tissue-specific and inducible, are known to those skilled in the art and can be utilized in the present invention. Typically, preferred promoters to use in the present invention are those that are induced by heat or low water conditions Such as the RD29a promoter (Kasuga et al., *Plant Cell Physiol.* 45:346 (2004) and Yamaguchi-Shinozaki and Shinozaki, *Mol Gen Genet.* 236: 331 (1993)) or other DRE-containing (dehydration-responsive elements) promoters (Liu et al, Cell 10: 1391 (1998)). Another preferred embodiment of the present invention is the use of root specific promoters such as those present in the ATXTH17, ATXTH18, AtXTH19 and AtXTH20 genes of *Arabidopsis* (Vissenberg et al. (2005) *Plant Cell Physiol* 46:192) or guard cell specific promoters such as TGG1 or KST1 (Husebye et al. (2002) *Plant Physiol* 128:1180; Plesch et al. (2001) *Plant J* 28:455).

Alternatively, misexpression can be accomplished using a two component system, whereby the first component comprises a transgenic plant comprising a transcriptional activator operatively linked to a promoter and the second component comprises a transgenic plant comprising a sequence of the invention operatively linked to the target binding sequence/region of the transcriptional activator. The two transgenic plants are crossed and the sequence of the invention is expressed in their progeny. In another alternative, the misexpression can be accomplished by transforming the sequences of the two component system into one transgenic plant line.

Any promoter that functions in plants can be used in the first component, such as those discussed above. Suitable transcriptional activator polypeptides include, but are not limited to, those encoding HAP1 and GAL4. The binding sequence recognized and targeted by the selected transcriptional activator protein (e.g. a UAS element) is used in the second component.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al., *Ann. Rev. Genet.* 22:421 (1988); and Christou, Euphytica, v. 85, n.1-3:13-27, (1995).

Processes for the transformation and regeneration of monocotyledonous and dicotyledonous plants are known to the person skilled in the art. For the introduction of DNA into a plant host cell a variety of techniques is available. These techniques include transformation of plant cells by injection (e.g. Newell, 2000), microinjection (e.g. Griesbach (1987) *Plant Sci.* 50 69-77), electroporation of DNA (e.g. Fromm et al. (1985) *Proc. Natl. Acad. Sci USA* 82:5824 and Wan and Lemaux, Plant Physiol. 104 (1994), 37-48), PEG (e.g. Paszkowski et al. (1984) *EMBO J.* 3:2717), use of biolistics (e.g. Klein et al. (1987) *Nature* 327:773), fusion of cells or protoplasts (Willmitzer, L., 1993 Transgenic plants. In: Biotechnology, A Multi-Volume Comprehensive Treatise (H. J. Rehm, G. Reed, A. Pühler, P. Stadler, eds., Vol. 2, 627-659, VCH Weinheim-New York-Basel-Cambridge), via T-DNA using *Agrobacterium tumefaciens* (e.g. Fraley et al. (Crit. Rev. Plant. Sci. 4, 146 and Fromm et al., Biotechnology 8 (1990), 833-844) or *Agrobacterium rhizogenes* (e.g. Cho et al. (2000) *Planta* 210:195-204) or other bacterial hosts (e.g. Brootghaerts et al. (2005) Nature 433:629-633), as well as further possibilities.

In addition, a number of non-stable transformation methods well known to those skilled in the art may be desirable for the present invention. Such methods include, but are not limited to, transient expression (e.g. Lincoln et al. (1998) *Plant Mol. Biol. Rep.* 16:14) and viral transfection (e.g. Lacomme et al. (2001) In "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to heat and/or low water conditions, without reduction in fertility, on essentially any plant.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The method of the invention is preferably used with plants that are interesting for agriculture, horticulture, biomass for bioconversion and/or forestry. Examples are tobacco, oilseed rape, sugar beet, potato, tomato, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

Homologs Encompassed by the Invention

Agents of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. The amino acid changes may be achieved by changing the codons of the nucleic acid sequence.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs (see below). Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of those sequences present in the Sequence Listing due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

5. Experiments Confirming the Usefulness of the Polynucleotides and Polypeptides of the Invention 5.1 Procedures The nucleotide sequences of the invention were identified by use of a variety of screens for pH and/or low phosphate and/or low nitrogen conditions. These screens are recognized by those skilled in the art to be predictive of nucleotide sequences that provide plants with improved tolerance to pH and/or low phosphate and/or low nitrogen conditions because they emulate the different environmental conditions that can result from increased pH and/or low phosphate and/or low nitrogen conditions. These screens generally fall into two categories (1) soil screens and (2) in vitro screens.

Soil screens have the advantage of assaying the response of the entire plant to particular conditions, such as high pH or low phosphorus. On the other hand, in vitro screens have the advantage of relying on defined media and so allow more defined manipulation of growth conditions. Each of the screens used is described in more detail below.

In general, the screens used to identify the polynucleotides and polypeptides of the invention were conducted using superpools of *Arabidopsis* $T_2$ transformed plants. The $T_1$ plants were transformed with a Ti plasmid containing a particular SEQ ID NO in the sense orientation relative to a constitutive promoter and harboring the plant-selectable marker gene phosphinothricin acetyltansferase (PAT), which confers herbicide resistance to transformed plants. For in vitro screens, seed from multiple superpools (1,200 $T_2$ seeds from each superpool) were usually tested. $T_3$ seed were collected from the resistant plants and retested on one or more in vitro screens. The results of the screens conducted for each SEQ ID NO can be found in the Examples below.

1. High pH

Screens for high pH resistance identify seedlings better able to thrive under nutritional deficiencies (e.g. Phosphate, Manganese, Iron, Boron) imposed by alkaline conditions.

Seeds are sterilized in 50% household bleach for 5 minutes and then washed with double distilled deionized water three times. Sterilized seed is stored in the dark at 4° C. for a minimum of 3 days before use.

High pH media is prepared by mixing 0.5 g/l MES hydrate with 1×MS+0.5% Sucrose. Prior to autoclaving pH is adjusted with 10 N KNH to the following values: pH 5.7 (control), pH 7.03, pH 8.02, pH 9.01 and pH 10.18. The media pH is retested since pH values drop after autoclaving as follows: pH 5.7→pH 5.66; pH 7.03→pH6.50; pH 8.02→pH 7.50; pH 9.01→pH 8.91; pH10.18→pH 9.91. Generally speaking, pH 9.01(pH 8.91) allows germination but no growth beyond 2 to 5 mm and no root growth. Germination does not occur at higher pH (e.g. pH 10.81).

Approximately 1200 seeds are evenly spaced per MS-sucrose plate before incubating in the vertical position at 22° C. for 14 days. Under these conditions, the plates are exposed to 12,030 LUX from above and 3,190 LUX from the bottom.

Seedlings are scored for root and shoot growth after 7 and 14 days. Putative tolerant seedlings are transferred to MS pH 5.7 for recovery for 14 days prior to transplanting in soil. Finale™ spraying is done after plants are moved to soil to remove non-transgenics from the population.

DNA is isolated from each $T_2$ plant and used in PCR reactions using the following cycling conditions: 95° C. for 5 min, 35 cycles of (94° C. for 30 sec, then 59° C. for 30 sec, then 72° C. for 1 min), 72° C. for 8 min and 4° C. hold. Aliquots of the reaction product are analyzed on a 1.0% agarose gel stained with ethidium bromide. The DNA products are sequenced to determine which insert sequences were in each superpool candidate chosen in the screen.

$T_3$ Seed from those plants containing sequenced PCR products are collected and retested on high pH media. In addition, plants are tested on MS media lacking Phosphate and having a pH of 5.7.

2. Zero Phosphate

Screens for zero phosphate tolerance identify seedlings better able to thrive under a phosphate nutritional deficiency.

Seeds are sterilized in 50% household bleach for 5 minutes and then washed with double distilled deionized water three times. Sterilized seed is stored in the dark at 4° C. for a miniumum of 3 days before use.

Zero phosphate media is prepared using commercially available MS media lacking phosphate, pH 5.7.

Approximately 1200 seeds are evenly spaced per MS-P plate before incubating in the vertical position at 22° C. for 14 days. Under these conditions, the plates are exposed to 12,030 LUX from above and 3,190 LUX from the bottom.

Seedlings are scored for root and shoot growth after 7 and 14 days. Putative tolerant seedlings are transferred to MS pH 5.7 for recovery for 14 days prior to transplanting in soil. Finale™ spraying is done after the plants are moved to soil to remove non-transgenics from the population.

DNA is isolated from each $T_2$ plant and used in PCR reactions using the following cycling conditions: 95° C. for 5 min, 35 cycles of (94° C. for 30 sec, then 59° C. for 30 sec, then 72° C. for 1 min), 72° C. for 8 min and 4° C. hold. Aliquots of the reaction product are analyzed on a 1.0% agarose gel stained with ethidium bromide. The DNA products are sequenced to determined which insert sequences were in each superpool candidate chosen in the screen.

$T_3$ Seed from those plants containing the sequenced PCR products are collected and retested.

3. Zero Phosphate, Zero Nitrogen

Screens for zero phosphate, zero nitrogen tolerance identify seedlings better able to thrive under a phosphate nutritional deficiency.

Seeds are sterilized in 50% household bleach for 5 minutes and then washed with double distilled deionized water three times. Sterilized seed is stored in the dark at 4° C. for a miniumum of 3 days before use.

Zero phosphate, zero nitrogen media is prepared using commercially available MS media lacking phosphate, pH 5.7.

Approximately 1200 seeds are evenly spaced per MS–P–N plate before incubating in the vertical position at 22° C. for 14 days. Under these conditions, the plates are exposed to 12,030 LUX from above and 3,190 LUX from the bottom.

Growth and overall greenness are assayed 10 days post-treatment. Seedling recovery is assessed by adding a thin layer (8.3 ml) of complete MS+P+N media, pH 5.7, softened by the addition of 0.02% agar. Media is added to the edge of the plate and slowly rotated until a thin film of +PN media is present on top of the solidified –PN media. Putative tolerant seedlings are greener and have increased growth compared to controls. Finale™ spraying is done after the plants are moved to soil to remove non-transgenics from the population.

DNA is isolated from each $T_2$ plant and used in PCR reactions using the following cycling conditions: 95° C. for 5 min, 35 cycles of (94° C. for 30 sec, then 59° C. for 30 sec, then 72° C. for 1 min), 72° C. for 8 min and 4° C. hold. Aliquots of the reaction product are analyzed on a 1.0% agarose gel stained with ethidium bromide. The DNA products are sequenced to determined which insert sequences were in each superpool candidate chosen in the screen.

$T_3$ Seed from those plants containing the sequenced PCR products are collected and retested.

5.2 Results

The results of the above experiments are set forth below wherein each individual example relates to all of the experimental results for a particular polynucleotide/polypeptide if the invention.

EXAMPLE 1

Ceres cDNA 12335629

Clone 40781, Ceres cDNA 12335629, encodes a full-length protein with homology to a ferredoxin thioredoxin reductase from *Arabidopsis thaliana*.

Ectopic expression of Ceres cDNA 12335629 under the control of the CaMV35S promoter induces the following phenotypes:
  Better growth and recovery after exposure to high pH conditions and
  Continued growth under high pH induced phosphate and iron deficiencies.

Generation and Phenotypic Evaluation of $T_1$ Lines Containing 35S::cDNA 12335629.

Wild-type *Arabidopsis* Wassilewskija (WS) plants were transformed with a Ti plasmid containing cDNA 12335629 in the sense orientation relative to the 35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High pH Media for pH Tolerance.

Seed from superpools of the 35S over-expression lines were evaluated for greenness and size on high pH media as described above. Once cDNA 12335629 was identified in tolerant plants, the five individual $T_2$ events containing this cDNA (ME03527) were screened on high pH media essentially as described above, but where the media pH is 8.5, to identify events with the tolerant phenotype.

Results:

Qualitative Analysis of the Superpool Containing 35S::Clone 40781 Plants on High pH The screen resulted in a decrease in germination and/or growth for both wildtype and superpools as compared to seeds on control media. Only one line survived transplantation to soil. The candidate was greener than controls but overall size was comparable to those of wild-type. There was no delay in flowering time or decrease in seed set in comparison to un-treated wild-type but a faster flowering time and greater seed set was apparent when compared to a recovered pH treated wild-type plant (data not shown). These results are consistent with those of the $T_1$ generation which displayed normal flowering time and fertility.

Qualitative and Quantitative Analysis of $T_3$-cDNA 12335629 on High pH.

The plants were treated with Finale™ to eliminate any false-positives or any lines where the Finale™ marker was suppressed. All of the Finale™-resistant candidates flowered and set seed. Finale™ segregation was assessed to identify events containing a single insert segregation in a 3:1 (R:S) ratio as calculated by chi-square test. All of the events segregated for a single functional insert (Table 1-1). The transgenic plants were greener and slightly larger than the control under high pH stress.

TABLE 1-1

Observed and expected frequencies assuming a 3:1 ratio for high pH tolerance of cDNA 12335629 progeny under high pH (pH 8.5). α of 0.05

| Event | Generation | Observed | Expected | $\chi^2$ | Probability of Chi-Test |
|---|---|---|---|---|---|
| pH Resistant | $T_3$ | 22 | 29 | 0.926 | |
| pH Sensitive | $T_3$ | 14 | 7 | 2.778 | 0.054 |
| N = 36 | | 36 | 36 | 3.704 | |

Qualitative and Quantitative Analysis of cDNA 12335629 Progeny on Media Lacking Phosphate Before testing independent $T_2$ events, plants containing cDNA 12335629 were re-assayed for phosphate starvation tolerance by growth on media containing no phosphate as described above. After seven days only slightly more tolerance compared to controls is observed, but cDNA 12335629 seedlings are a bit larger and slightly greener than those of the control. Because the slight increase in size was particularly difficult to assess, anything lower or equal to the wild-type average of 0.42 cm was assessed to be sensitive and anything higher was assessed as tolerant. Twenty-four resistant and twelve phosphate starved sensitive seedlings were compared to Finale™ frequencies and found to have a Chi-test probability of 0.49, suggesting a positive fit (Table 1-2).

TABLE 1-2

Observed and expected frequencies assuming a 3:1 ratio for phosphate starvation tolerance among progeny of cDNA 12335629 media lacking phosphate (−P). α of 0.05

| Event | Generation | Observed | Expected | $\chi^2$ | Probability of Chi-Test |
|---|---|---|---|---|---|
| −P Resistant | $T_3$ | 24 | 27 | 0.333 | |
| −P Sensitive | $T_3$ | 12 | 9 | 1.333 | 0.25 |
| N = 36 | | 36 | 36 | 1.666 | |

Qualitative and Quantitative Analysis of Individual $T_2$ Events of cDNA 12335629 on High pH Plate Assay.

Five individual events of cDNA 12335629 (ME03527) were analyzed for a positive phenotype under high pH conditions. All five $T_2$ events had wild-type germination frequencies on MS pH 5.7 plates (data not shown). All $T_2$ lines and recovered $T_3$ lines showed evidence of a single insert as determined by Chi-square analysis (Table 1-3). Seeds from each of the five independent $T_2$ events, were plated on pH 8.5 plates and allowed to germinate and grow for 14 days.

Four of five $T_2$ events of ME03527 (-02, -03, -04, and -05) had a positive high pH tolerance phenotype as defined by growth and greenness. The phenotype of ME03527-01 was too weak to assess as positive compared to the controls (Table 1-4). Phenotype strength varied among the four positive independent events, but all showed better growth than controls. The segregation ratios, determined by a Chi-square test, show that the segregation of the transgene is the same as observed for Finale™ (Table 1-4). ME03527-02, -03, -04, and -05 had the strongest and most consistent pH tolerance phenotypes.

TABLE 1-3

Observed and expected frequencies assuming a 3:1 (R:S) ratio for Finale ™ resistance among 35S::clone 40781 $T_2$ and $T_3$ events tested for growth under high pH conditions. α of 0.05

| Event | Generation | Observed | Expected | $\chi^2$ | Probability of Chi-Test |
|---|---|---|---|---|---|
| ME03527-01 Finale ™ Resistant | $T_2$ | 16 | 18 | 0.222 | |
| ME03527-01 Finale ™ Sensitive | $T_2$ | 8 | 6 | 0.667 | 0.35 |
| N = 24 | | 24 | 24 | 0.889 | |
| ME03527-02 Finale ™ Resistant | $T_2$ | 28 | 27 | 0.037 | |
| ME03527-02 Finale ™ Sensitive | $T_2$ | 8 | 9 | 0.111 | 0.70 |
| N = 36 | | 36 | 36 | 0.148 | |
| ME03527-03 Finale ™ Resistant | $T_2$ | 17 | 18 | 0.056 | |
| ME03527-03 Finale ™ Sensitive | $T_2$ | 7 | 6 | 0.167 | 0.64 |
| N = 24 | | 24 | 24 | 0.223 | |
| ME03527-04 Finale ™ Resistant | $T_2$ | 27 | 27 | 0 | |
| ME03527-04 Finale ™ Sensitive | $T_2$ | 9 | 9 | 0 | 1.0 |
| N = 36 | | 36 | 36 | 0 | |
| ME03527-05 Finale ™ Resistant | $T_2$ | 23 | 27 | 0.593 | |
| ME03527-05 Finale ™ Sensitive | $T_2$ | 13 | 9 | 1.778 | 0.12 |
| N = 36 | | 36 | 36 | 2.371 | |

TABLE 1-3-continued

Observed and expected frequencies assuming a 3:1 (R:S) ratio for Finale ™ resistance among 35S::clone 40781 T$_2$ and T$_3$ events tested for growth under high pH conditions. α of 0.05

| Event | Generation | Observed | Expected | $\chi^2$ | Probability of Chi-Test |
|---|---|---|---|---|---|
| cDNA 12335629 Finale ™ Resistant | T$_3$ | 22 | 27 | 0.926 | |
| cDNA 12335629 Finale ™ Sensitive | T$_3$ | 14 | 9 | 2.778 | 0.054 |
| N = 36 | | 36 | 36 | 3.704 | |

TABLE 1-4

Observed and expected frequencies of high pH tolerance assuming segregation of transgene is the same as observed in Finale ™ resistance among 35S::clone 40781 T$_2$ and T$_3$ events that showed increased growth under high pH conditions. α of 0.05

| Event | Generation | Observed | Expected | $\chi^2$ | Probability of Chi-Test |
|---|---|---|---|---|---|
| ME03527-01 pH Resistant | T$_2$ | 15 | 25.5 | 4.324 | |
| ME03527-01 pH Sensitive | T$_2$ | 19 | 85.5 | 2.970 | 32E−05 |
| N = 36 | | 34 | 34 | 7.294 | |
| ME03527-02 pH Resistant | T$_2$ | 23 | 24.75 | 0.124 | |
| ME03527-02 pH Sensitive | T$_2$ | 10 | 8.25 | 0.371 | 0.48 |
| N = 36 | | 33 | 33 | 0.495 | |
| ME03527-03 pH Resistant | T$_2$ | 23 | 23.25 | 0.003 | 0.92 |
| ME03527-03 pH Sensitive | T$_2$ | 8 | 7.75 | 0.008 | |
| N = 36 | | 31 | 31 | 0.011 | |
| ME03527-04 pH Resistant | T$_2$ | 24 | 27 | 0.333 | 0.25 |
| ME03527-04 pH Sensitive | T$_2$ | 12 | 9 | 1.000 | |
| N = 36 | | 36 | 36 | 1.333 | |
| ME03527-05 pH Resistant | T$_2$ | 19 | 27 | 2.370 | 0.002 |
| ME03527-05 pH Sensitive | T$_2$ | 17 | 9 | 7.111 | |
| N = 36 | | 36 | 3 | 9.481 | |
| cDNA 12335629 pH Resistant | T$_3$ | 19 | 27 | 2.370 | 0.002 |
| cDNA 12335629 pH Sensitive | T$_3$ | 17 | 9 | 7.111 | |
| N = 36 | | 36 | 36 | 9.481 | |

Table 1-5 provides the results of the consensus sequence analysis based on Ceres cDNA 13487605 (CeresClone: 40781, SEQ ID NO:13). The amino acid sequence of Clone 40781 (SEQ ID NO:13) is aligned with homologous and/or orthologous amino acid sequences CeresClone:295783 (SEQ ID NO:18), gi|50898984 (SEQ ID NO:19), CeresClone: 470939 (SEQ ID NO:16), gi|14275859 (SEQ ID NO:17), gi|505189 (SEQ ID NO:14), CeresClone:1127455 (SEQ ID NO: 15), as well as with the consensus sequence (SEQ ID NO: 50-54), in all the alignment figures shown herein, a dash in an aligned sequence represents a gap, i.e., a lack, of an amino acid at that position. Identical amino acids or conserved amino acid substitutions among aligned sequences are identified by boxes. Alignment shown in Table 1-5 and the other alignment figures provided herein were generated using the program MUSCLE version 3.52.

TABLE 1-5

```
CeresClone:295783   MTSTVITTVG  CGGLPVRPLS  TATRGRPRRC  AVRAQ--AAG  ADASNDKSVE   48
gi|50898984         MMSMASTT--  ------ASPFC  PSPMPRGRKC  TVRVQAGAAG  ADAS-DKSLE   42
CeresClone:470939   MTTQASTFAV  AVPSVATPF-  ---RRHRNPF  VVRAQ-----  AEPS-DKSVE   40
gi|14275859         MRTLQASTSY  SVGFGISSFA  TRPKPSTHRC  LTVAK-----  MEPS-EKSVE   44
gi|505189           MKALQASTSY  SFFSKSSSAT  LQRRTHRPQC  VILSK-----  VEPS-DKSVE   44
Lead•clone40781     MNLQAVSCSF  GFL--SSPLG  VTPRTSFRRF  VIRAK-----  TEPS-EKSVE   42
CeresClone:1127455  MNPQAVSCSF  GFV--SAPL-  VSPRTS--RF  VVQAK-----  SEPS-EXSVE   39

Concensus           M---A-TTS-  ------ASP--  -SPR----RC  VVRAK-----  -EPS-DKSVE   50
```

TABLE 1-5-continued

| | | | | | | | |
|---|---|---|---|---|---|---|---|
| CeresClone:295783 | VMRKFSEQYA | RRSNTFFCAD | KTVTAVVIKG | LADHRDTLGA | PLCPCRHYDD | | 98 |
| gi\|50898984 | IMRKFSEQYA | RRSNTFFCSE | KSVTAVVIKG | LADHKDQLGA | PLCPCRHYDD | | 92 |
| CeresClone:470939 | IMRKFSEQYA | RKSGTYFCVD | KGVTSVVIKG | LADHKDTLGA | PLCPCRHYDD | | 90 |
| gi\|14275859 | IMRKFSEQYA | RRSETYFCMD | KGVTSVVIKG | LAEHKDTLGA | PLCPCRHYDD | | 94 |
| gi\|505189 | IMRKFSEQYA | RKSGTYFCVD | KGVTSVVIKG | LAEHKDSLGA | PLCPCRHYDD | | 94 |
| Lead•clone40781 | IMRKFSEQYA | RRSGTYFCVD | KGVTSVVIKG | LAEHKDSYGA | PLCPCRHYDD | | 92 |
| CeresClone:1127455 | IMRKFSEQYA | RRSGTYFCVD | KGVXSVVIKG | LAEHKDSYGA | PLCPCRHYDD | | 89 |
| Concensus | IMRKFSEQYA | RRSGTYFCVD | KGVTSVVIKG | LADHKD-LGA | PLCPCRHYDD | | 100 |
| | | | | | | | |
| CeresClone:295783 | KAAEVAQGFW | NCPCVPMRER | KECHCMLFLT | PDNDFAGKDQ | VISFEEIKEA | | 148 |
| gi\|50898984 | KAAEVAQGFW | NCPCVPMRER | KECHCMLFLT | PDNDFAGQDQ | AITLEEIKDA | | 142 |
| CeresClone:470939 | KAAEVAQGFW | NCPCVPMRER | KECHCMLFLT | PDNDFAGNEQ | TITLDEIKES | | 140 |
| gi\|14275859 | KAAEAQQGFW | NCPCVPMRER | KECHCMLFLT | PDNDFAGEEQ | TISMEEIKET | | 144 |
| gi\|505189 | KAAEATQGFW | NCPCVPMRER | KECHCMLFLT | PENDFAGKDQ | TIGLDEIREV | | 144 |
| Lead•clone40781 | KAAEVGQGFW | NCPCVPMRER | KECHCMLFLT | PDNDFAGKDQ | TITSDEIKET | | 142 |
| CeresClone:1127455 | KAAEVGQGFW | NCPCVPMRER | KECHCMLFLT | PDNDFAGKDQ | TITSDEIKET | | 139 |
| Concensus | KAAEV-QGFW | NCPCVPMRER | KECHCMLFLT | PDNDFAGKDQ | TITLDEIKE- | | 150 |
| | | | | | | | |
| CeresClone:295783 | TSKF | | | | | | 152 |
| gi\|50898984 | TSKI | | | | | | 146 |
| CeresClone:470939 | TANM | | | | | | 144 |
| gi\|14275859 | TANM | | | | | | 148 |
| gi\|505189 | TANM | | | | | | 148 |
| Lead•clone40781 | TANM | | | | | | 146 |
| CeresClone:1127455 | TAHM | | | | | | 143 |
| Concensus | TANM | | | | | | 154 |

EXAMPLE 2

Ceres cDNA 12330185

Clone 34035, Ceres cDNA 12330185, encodes a 128 amino acid protein of unknown function (DUF423) from *Arabidopsis thaliana*.

Ectopic expression of Ceres cDNA 12330185 under the control of the 32449 promoter induces the following phenotypes:

Increased size and greenness on nutrient deficiencies incurred by high pH conditions, Better soil recovery after exposure to high pH stress, and Better recovery after exposure to conditions lacking both phosphate and nitrogen.

Generation and Phenotypic Evaluation of $T_1$ Lines Containing p32449::cDNA 12330185.

Wild-type *Arabidopsis* Wassilewskija (WS) plants were transformed with a Ti plasmid containing cDNA 12330185 in the sense orientation relative to the 32449 constitutive promoter. Promoter 32449 has broad expression throughout *Arabidopsis*, although at much lower expression level than CaMV35S. The $T_i$ plasmid vector used for this construct, CRS311, contains PAT and confers herbicide resistance to transformed plants. Nine independently transformed events were selected and evaluated for their qualitative phenotype in the $T_1$ generation. No positive or negative phenotypes were observed in the $T_1$ plants.

Screens of Superpools on High pH Media for pH Tolerance.

Seed from superpools of the 32449 over-expression lines were evaluated for greenness and size on high pH media as described above. Once cDNA 12330185 was identified in tolerant plants, nine individual $T_2$ events containing this cDNA (ME00077) were screened on high pH media essentially as described above, but where the media pH is 8.5, to identify events with the tolerant phenotype.

Results:

Qualitative Analysis of the Superpool Containing 34449::cDNA 12330185 on High pH The cDNA 12330185 line displayed a delayed flowering time of ~8 days and decreased seed set in comparison to the un-treated wild-type. However cDNA 12330185 displayed a faster flowering time (~15 days) and greater seed set when compared to the high pH grown wild-type plant.

Qualitative and Quantitative Analysis of the $T_3$ 32449::cDNA 12330185 on High pH.

The cDNA 12330185 line was tested for Finale™ resistance and re-assayed for continued pH tolerance. The segregation ratio of $T_3$ seeds from cDNA 12330185 is suggestive of a single insert, as calculated by a Chi-square test (Table 2-1). The cDNA 12330185 line was re-tested on pH 9.0 media as described and found to be tolerant to high pH when compared to controls.

TABLE 2-1

Chi-square analysis of progeny of cDNA 12330185 on Finale ™ assuming a 3:1 ratio.

| Event | Observed | Expected | $\chi^2$ | Probability of Chi-Test |
|---|---|---|---|---|
| Finale ™ Resistant | 27 | 27 | 0 | |
| Finale ™ Sensitive | 9 | 9 | 0 | 1 |
| N = 36 | 36 | 36 | 0 | |

Qualitative and Quantitative Analysis of Phosphate and Nitrate Starvation of $T_3$ (cDNA 12330185) Plants.

To ascertain whether the pH tolerant phenotype is related to better survival under nutrient starvation, $T_3$ seeds were assayed on MS media lacking both phosphate (−P) and nitrate (−N) (pH 5.7) as described above. The cDNA 12330185 line was greener and of equal size compared to wild-type controls. Ten days after the addition of +NP media film, cDNA 12330185 seedlings recovered more quickly than wild type. Twenty-five of 36 seedlings of SP9pH1 had greater growth when compared to wild type. This increased growth frequency is suggestive of a single insert as determined by Chi-square analysis (Table 2-2).

TABLE 2-2

Observed and expected frequencies of no phosphate/nitrate growth assuming segregation of transgene is 3:1 (R:S) of $T_3$ plants of cDNA 12330185 that showed increased growth under high pH conditions. α of 0.05

| Event | Observed | Expected | $\chi^2$ | Probability of Chi-Test |
|---|---|---|---|---|
| −NP Resistant | 25 | 27 | 0.148 | 0.441 |
| −NP Sensitive | 11 | 9 | 0.444 | |
| N = 36 | 36 | 36 | 0.592 | |

Qualitative and Quantitative Analysis of Individual $T_2$ Events of cDNA 12330185 on High pH.

Seeds from $T_2$ lines representing nine individual events and containing cDNA 12330185 (ME0077-01, 02, 03, 04, 05, 06, 07, 08, 09) were plated on pH media, pH 8.5 as described above. Plates were evaluated at 7 and 12 days post-plating (Table 2-3). All nine $T_2$ events had wild-type germination frequencies except for ME00077-04 (Table 2-4). This germination problem however was not observed when seedlings were plated onto high pH plates.

Six of the nine events showed tolerance to high pH as defined by growth and greenness. The strongest tolerance phenotypes were in ME00077-03 and ME00077-05. ME00077-03 and ME00077-05 both had single inserts as determined by Chi-square analysis (Table 2-3).

The pH tolerant phenotype was strongest in the cDNA 12330185 $T_3$ line recovered from the superpool screen. We did not do a genetic mapping of this line's insert to determine which event it represented. This line's phenotype was so strong that it allowed adjacent wild-type quadrants within same plate to grow normally after 14-days. This is most likely due to acidification of surrounding media by the pH tolerant line. ME00077-03, -05 $T_2$ plants also showed increased recovery during phosphate and nitrogen starvation assays (data not shown). However, the cDNA 12330185 $T_3$ line recovered from the superpool phenotype was stronger than that observed for lines ME00077-03 and -05 under −NP starvation recovery (as noted above).

TABLE 2-3

Observed and expected frequencies assuming a 3:1 (R:S) or 15:1 (R:S) ratio for Finale ™ among progeny of 32449:: cDNA 12330185T$_2$ and T$_3$ events tested for growth under high pH conditions. α of 0.05. Shading signifies a fit for 3 to 1.

| Event | Generation | Observed | Expected | $\chi^2$ | Probability of Chi-Test | pH Phenotype |
|---|---|---|---|---|---|---|
| ME00077-01 Finale™ Resistant | $T_2$ | 34 | 33.75 | 0.002 | | |
| ME00077-01 Finale™ Sensitive | $T_2$ | 2 | 2.25 | 0.028 | 0.86 | No |
| N = 36 | | 36 | 36 | 0.030 | 15R:1 | |
| ME00077-01 Finale™ Resistant | $T_3$ | 34 | 31.875 | 0.142 | | |
| ME00077-01 Finale™ Sensitive | $T_3$ | 0 | 2.125 | 2.125 | 0.13 | No |
| N = 36 | | 34 | 34 | 2.267 | 15R:1S | |
| ME00077-02 Finale™ Resistant | $T_2$ | 32 | 30.938 | 0.036 | | |
| ME00077-02 Finale™ Sensitive | $T_2$ | 1 | 2.062 | 0.547 | 0.44 | No |
| N = 36 | | 33 | 33 | 0.583 | 15R:1S | |
| ME00077-02 Finale™ Resistant | $T_3$ | 36 | 33.75 | 0.15 | | |
| ME00077-02 Finale™ Sensitive | $T_3$ | 0 | 2.25 | 2.25 | 0.12 | No |
| N = 36 | | 36 | 36 | 2.4 | 15R:1S | |
| ME00077-03 Finale™ Resistant | $T_2$ | 30 | 26.25 | 0.536 | | |
| ME00077-03 Finale™ Sensitive | $T_2$ | 5 | 8.75 | 1.607 | 0.143 | Yes |
| N = 17 | | 35 | 35 | 2.143 | 3R:1S | Strong |
| ME00077-04 Finale™ Resistant | $T_2$ | 19 | 18 | 0.0556 | | |
| ME00077-04 Finale™ Sensitive | $T_2$ | 5 | 6 | 0.1667 | 0.64 | Yes |
| N = 36 | | 24 | 24 | 0.2222 | 3R:1S | Low |
| ME00077-05 Finale™ Resistant | $T_2$ | 24 | 25.5 | 0.088 | | |
| ME00077-05 Finale™ Sensitive | $T_2$ | 10 | 8.5 | 0.265 | 0.552 | Yes |
| N = 36 | | 34 | 34 | 0.353 | 3R:1S | Strong |
| ME00077-06 Finale™ Resistant | $T_2$ | 30 | 26.25 | 0.536 | | |
| ME00077-06 Finale™ Sensitive | $T_2$ | 5 | 8.75 | 1.607 | 0.143 | Yes |
| N = 36 | | 35 | 35 | 2.143 | 3R:1S | Low |
| ME00077-07 Finale™ Resistant | $T_2$ | 32 | 31.875 | 0.0005 | | |
| ME00077-07 Finale™ Sensitive | $T_2$ | 2 | 2.125 | 0.007 | 0.093 | No |
| N = 36 | | 34 | 34 | 0.0075 | 15R:1S | |
| ME00077-08 Finale™ Resistant | $T_2$ | 30 | 26.25 | 0.536 | | |
| ME00077-08 Finale™ Sensitive | $T_2$ | 5 | 8.75 | 1.607 | 0.143 | Yes |
| N = 36 | | 35 | 35 | 2.143 | 3R:1S | Strong |
| ME00077-09 Finale™ Resistant | $T_2$ | 30 | 26.25 | 0.536 | | |
| ME00077-09 Finale™ Sensitive | $T_2$ | 5 | 8.75 | 1.607 | 0.143 | Yes |
| N = 36 | | 35 | 35 | 2.143 | 3R:1S | |
| cDNA 12330185 Finale™ Resistant | $T_3$ | 27 | 27 | 0 | | |
| cDNA 12330185 Finale™ Sensitive | $T_3$ | 9 | 9 | 0 | 1 | Yes |
| N = 36 | | 36 | 36 | 0 | 3R:1S | Strong |

TABLE 2-4

Observed germination frequencies on Finale ™ plates among progeny of 32449:: cDNA 12330185 $T_2$ and $T_3$ events tested for growth under high pH conditions.

| Events of 32449::clone 34035 | Generation | N | % Germination on Finale™ |
|---|---|---|---|
| Internal pH Wild-type Control | T3 | 36 | 100 |
| ME00077-01 | T2 | 36 | 100 |
| ME00077-01-01 | T3 | 36 | 94 |
| ME00077-02 | T2 | 36 | 92 |
| ME00077-02-01 | T3 | 36 | 100 |
| ME00077-03 | T2 | 17 | 100 |
| ME00077-04** | T2 | 36 | 67 |
| ME00077-05 | T2 | 36 | 94 |
| ME00077-06 | T2 | 36 | 97 |
| ME00077-07 | T2 | 36 | 92 |
| ME00077-08 | T2 | 36 | 97 |
| ME00077-09 | T2 | 36 | 97 |
| cDNA 12330185 | T3 | 36 | 100 |

**Germination reduction in comparison to wild-type control and other ME00077 lines

TABLE 2-5

Observed and expected frequencies of high pH tolerance assuming segregation of transgene is the same as observed in Finale ™ segregation among progeny of 32449:: cDNA 12330185 $T_2$ events that showed increased growth under high pH conditions. α of 0.05

| Event | Observed | Expected | $\chi^2$ | Probability of Chi-Test |
|---|---|---|---|---|
| ME00077-03 pH Resistant | 26 | 25.5 | 0.009 | 0.84 |
| ME00077-03 pH Sensitive | 8 | 8.5 | 0.029 | |
| N = 36 | 34 | 34 | 0.038 | |
| ME00077-05 pH Resistant | 29 | 26.25 | 0.288 | 0.28 |
| ME00077-05 pH Sensitive | 6 | 8.75 | 0.864 | |
| N = 36 | 35 | 35 | 1.152 | |
| cDNA 12330185 pH Resistant | 31 | 27 | 0.592 | 0.124 |
| cDNA 12330185 pH Sensitive | 5 | 9 | 1.778 | |
| N = 36 | 36 | 36 | 2.370 | |

Table 2-6 provides the results of the consensus sequence analysis based on Ceres cDNA 12330185 (CeresClone: 34035, SEQ ID NO:2). The amino acid of Clone:34035 (SEQ ID NO:2) is aligned with homologous and/or orthologous amino acid sequences CeresClone:566573 (SEQ ID NO:5), CeresClone:588155 (SEQ ID NO:6), CeresClone:289088 (SEQ ID NO:8), gi|50918749 (SEQ ID NO: 11) gi|7963694 (SEQ ID NO:9), CeresClone:678257 (SEQ ID NO:7), gi|7963702 (SEQ ID NO:10), CeresClone:972918 (SEQ ID NO:4), CeresClone:872428 (SEQ ID NO:3), as well as with the consensus sequence (SEQ ID NO:55-60).

TABLE 2-6

```
CeresClone:566573   ----------  -------MDP  QLWHKVAAIS  GLAALGLGTY  GAHVFKPQNP   33
CeresClone:588155   ----------  -------MDP  QVWHKVAAIS  GVAALGLGTY  GAHVFKPQNP   33
CeresClone:289088   ----------  ---MLAATDP  MLWHKVAAVS  GVAALGLGTY  GAHMFRPKNP   37
gi|50918749         --------MA  AAAAMAMKDP  SLWHKVAAIS  GVAALGLGTY  GAHMFRPKNP   42
gi|7963694          ----------  ----------  MLWHKVAAVS  GVAALGLGTY  GAHMFRPQNP   30
CeresClone:678257   ----------  ---MVMPTDP  MLWHKVAAVS  GVVALGLGTY  GAHMFRPQNP   37
gi|7963702          ----------  ---MVMPTDP  MLWHKVAAVS  GVAALGLGTY  GAHMFRPQNP   37
CeresClone:972918   MGNCVRSNLR  DLGGRRSMDP  RIWHKVAAIS  GMAALGLGTY  GAHVFKPENP   50
Lead•Clone34035     MGNSVRSNLR  DIRGRRSMDP  RMWHKVAAIS  GMAALGLGTY  GAHVFKPENP   50
CeresClone:872428   ----------  -------MDP  RIWHKVAAVS  GMAALGLGTY  GAHVFKPENP   33

Consensus           ----------  -------MDP  RLWHKVAAVS  GVAALGLGTY  GAH-F-PQNP   50

CeresClone:566573   AYNDVWHTAS  LYHLVHTAAL  VAAPITKHPN  VFGGLLTAGI  LAFSGTCYTV   83
CeresClone:588155   AYKDVWHTAS  LYHLVHTAAL  VAAPITKHPN  VFGGLLTAGI  LAFSGTCYTV   83
CeresClone:289088   AYKEVWHTAS  LYHLVHTAAL  LGAPITKRPN  VFGGLLTAGI  VLFSGTCYTV   87
gi|50918749         AYKEVWHTAS  LYHLVHTAAL  LGAPITKRPD  VFGGLLTAGI  VLFSGTCYTV   92
gi|7963694          KYKEIWQTAF  LYHLVHTAAL  LGAPMTKRPN  IFGGLLTTGI  VLFSGTCYTV   80
CeresClone:678257   RYKEIWQTAS  LYHLVHTAAL  LGAPMTKRPN  IFGGLLTTGI  VLFSGTCYTV   87
gi|7963702          RYKEIWQTAS  LYHLVHTAAL  LGAPMTKRPN  IFGGLLTTGI  VLFSGTCYTV   87
CeresClone:972918   SYKQVWQTAS  LYHLVHTAAL  VSAPSTKYPN  IFGGLLTAGI  VAFSGT----   96
Lead•Clone34035     SYKQVWQTAS  LYHLVHTAAL  VSAPSTKYPN  IFGGLLTAGI  VAFSGTCYMV  100
CeresClone:872428   SYKQVWQTAS  LYHLVHTAAL  VSAPSTKYPN  IFGGLLTAGI  VAFSGTCYMV   83

Consensus           AYKEVWQTAS  LYHLVHTAAL  --APMTK-PN  IFGGLLTAGI  V-FSGTCYTV  100

CeresClone:566573   AFLEDRKYST  MAPFGGFAFI  AAWGSLFF--  ----------  ----------  111
CeresClone:588155   AFLEDRKYST  MAPFGGFAFI  AAWGSLFF--  ----------  ----------  111
CeresClone:289088   AYLEDRKFSS  PAPLGGFAFI  AAWASLLF--  ----------  ----------  115
gi|50918749         AYLEDRKYSS  TAPLGGFAFI  AAWASLLF--  ----------  ----------  120
gi|7963694          AYLEDRKFSS  PAP-------  ----------  ----------  ----------   93
CeresClone:678257   AYLEDRKFSS  PAPIGGFAFI  AAWASLLF--  ----------  ----------  115
gi|7963702          AYLEDRKFSS  PAPIGGFAF-  ----------  ----------  ----------  106
CeresClone:972918   -YEYAKSFVF  VNVVG-----  VTW-------  ----------  ----------  113
Lead•Clone34035     ALREDRKFST  LAPFGGFAFI  AAWATLLF--  ----------  ----------  128
CeresClone:872428   ALREDRKFST  LAPFGGFAFI  AAWATLLF--  ----------  ----------  111

Consensus           AYLEDRKFST  -AP-GGFAFI  AAWASLLF--  ----------  ----------  128
```

EXAMPLE 3

Ceres cDNA 12482777

Clone 126592, Ceres cDNA 12482777, encodes a full-length protein that has homology to an iron/manganese superoxide dismutase from *Arabidopsis thaliana*.

Ectopic expression of Ceres cDNA 12482777 under the control of the CaMV35S promoter induces the following phenotypes:

Increased growth under high pH induced stress
Better recovery after exposure to pH stress
Reduced height without a reduction in harvest index.

Generation and Phenotypic Evaluation of $T_1$ Lines Containing 35S::cDNA 12482777.

Wild-type *Arabidopsis* Wassilewskija (WS) plants were transformed with a Ti plasmid containing cDNA 12482777 in the sense orientation relative to the 35S constitutive promoter. The $T_i$ plasmid vector used for this construct, CRS338, contains PAT and confers herbicide resistance to transformed plants. Seven independently transformed events were selected and evaluated for their qualitative phenotype in the $T_1$ generation. No negative phenotypes were observed in the $T_1$ plants, although an increase in the number of branches was observed one of the events.

Screens of Superpools on High pH Media for pH Tolerance.

Seed from superpools of the 35S over-expression lines were evaluated for greenness and size on high pH media as described above. $T_3$ seed were also assayed for total seed yield, total tissue dry weight and harvest index as described above.

Results:

Qualitative Analysis of the Superpool Containing 35S::cDNA 12482777 Plants on High pH The screen identified a single event that was greener and the overall size was comparable to the controls. There was no delay in flowering time or decrease in seed set compared to un-treated wild-type. After recovery, the plant containing cDNA 12482777 had significantly better seed yield, as determined by seed volume, than controls (FIG. 2).

Qualitative and Quantitative Analysis of $T_3$-cDNA 12482777 on High pH.

The plants were treated with Finale™ to eliminate any false-positives or any lines where the Finale™ marker was suppressed. All of the Finale™-resistant candidates flowered and set seed. Finale™ resistance segregation in the $T_3$ line suggested a segregation ratio of 1:1 (R:S) as calculated by chi-square test (Table 3-1).

The plants were greener than the pre-pH treated control. There was no tolerant effect found under low phosphate conditions (data not shown), suggesting that the tolerant response is not to the nutrient deficiencies imposed by the high pH but rather to oxidative stress induced by alkalinity.

TABLE 3-1

Observed and expected frequencies assuming ratio for high pH tolerance among cDNA 12335629 tested for growth under high pH (pH 9.0) assuming a 3:1 (R:S) segregation ratio. α of 0.05

| Event | Generation | Observed | Expected | $\chi^2$ | Probability of Chi-Test |
|---|---|---|---|---|---|
| cDNA 12482777 pH Resistant | $T_3$ | 23 | 27 | 0.593 | |

TABLE 3-1-continued

Observed and expected frequencies assuming ratio for high pH tolerance among cDNA 12335629 tested for growth under high pH (pH 9.0) assuming a 3:1 (R:S) segregation ratio. α of 0.05

| Event | Generation | Observed | Expected | $\chi^2$ | Probability of Chi-Test |
|---|---|---|---|---|---|
| cDNA 12482777 pH Sensitive | $T_3$ | 13 | 9 | 1.778 | 0.12 |
| N = 36 | | 36 | 36 | 2.371 | |

Qualitative and Quantitative Analysis of Harvest Index, Seed Yield, and Plant Height of $T_3$ Progeny of 35S::cDNA 12482777.

A segregating population of 17 plants containing cDNA 12482777 was analyzed for harvest index and seed yield compared to wild-type populations. Based upon stem height measurements, the transgenic population of 35S::cDNA 12482777 (10 plants) was significantly smaller than both internal (6 plants) and external wild-type/control populations. Internal wild-types/controls were those plants segregating from the $T_3$ population of the 35S::cDNA 12482777 line which did not contain the insert (segregating non-transgenics). External wild-types were non-transgenic plants from an outside source which shared no lineage with the line being tested. External wild-types are added to the experiment as a process control to ensure the quality of the growth conditions. Average height for transgenic plants of cDNA 12482777 was 33.44 cm±0.78 versus 44.65 cm±0.70 for the internal wild-type controls. Despite this decrease in plant height, harvest index, as measured by seed weight/total plant weight remained unaffected, i.e., these transgenic plants still produced the same ratio of total seed weight:total plant weight (biomass) as non-transgenic controls. This result means that although the total seed yield is decreased in cDNA 12482777 lines, it still has the same seed proportionally as controls. The cDNA 12482777 plants had a harvest index of 56.96±2.99 compared to the wild-type population's harvest index of 44.92±2.67 (Table 3-2A). This increase in harvest index was significant at a P-value of 0.009 (Table 3-3A).

It is important to note that seed weight of cDNA 12482777 plants with a larger harvest index was 0.30977 g±0.025 while the wild-type population had an average seed weight of 0.37155 g±0.027 (Table 3-3B). cDNA 12482777 has a slightly smaller seed weight than the wild-type population but not statistically different at a P-value of 0.12 (Table 3-3B), suggesting that the harvest index of 35S::cDNA 12482777 is comparable to, if not greater than, wild-type plants. This increase in harvest index is not due to an increase in number of branches (data not shown) as observed in the $T_1$ generation. Instead, the internode length between siliques is reduced compared to the internal wild-type control, suggesting that cDNA 12482777 plants have more siliques per stem length.

TABLE 3-2A

Descriptive statistical comparison of Harvest Index between segregating $T_4$ populations containing cDNA 12482777.

| Harvest Index: cDNA 12482777 small stature | Transgenic Population | Harvest Index: of cDNA 12482777 Wild-type stature | Internal Wild-type Population |
|---|---|---|---|
| Mean | 56.9582619 | Mean | 44.91972222 |
| Standard Error | 2.990040579 | Standard Error | 2.667294901 |
| Median | 56.68809524 | Median | 45.56319444 |

TABLE 3-2A-continued

Descriptive statistical comparison of Harvest Index between segregating T₄ populations containing cDNA 12482777.

| Harvest Index: cDNA 12482777 small stature | Transgenic Population | Harvest Index of: cDNA 12482777 Wild-type stature | Internal Wild-type Population |
|---|---|---|---|
| Standard Deviation | 9.455338527 | Standard Deviation | 6.533511501 |
| Sample Variance | 89.40342666 | Sample Variance | 42.68677253 |
| Minimum | 43.41666667 | Minimum | 33.9375 |
| Maximum | 70.11666667 | Maximum | 54.36666667 |
| Sum | 569.582619 | Sum | 269.5183333 |
| Count | 10 | Count | 6 |
| Confidence Level (95.0%) | 6.763946869 | Confidence Level (95.0%) | 6.856488619 |

TABLE 3-2B

Descriptive statistical comparison of total seed weight (g) at time of harvest between segregating T₄ populations containing cDNA 12482777.

| Total Seed Weight (g) of: cDNA 12482777: Small Stature | Transgenic Population | Total Seed Weight (g) of: cDNA 12482777: Wild-type Stature | Internal Wild-type Population |
|---|---|---|---|
| Mean | 0.30977 | Mean | 0.37155 |
| Standard Error | 0.024799382 | Standard Error | 0.027304014 |
| Median | 0.3017 | Median | 0.3796 |
| Standard Deviation | 0.078422531 | Standard Deviation | 0.066880902 |
| Sample Variance | 0.006150093 | Sample Variance | 0.004473055 |
| Minimum | 0.1956 | Minimum | 0.2715 |
| Maximum | 0.4207 | Maximum | 0.4621 |
| Sum | 3.0977 | Sum | 2.2293 |
| Count | 10 | Count | 6 |
| Confidence Level (95.0%) | 0.056100142 | Confidence Level (95.0%) | 0.070187087 |

TABLE 3-4A

Statistical comparison of harvest index between transgenic populations of clone 126592 and internal wild-type populations using a t-test on two samples assuming unequal variances. cDNA 1248277 Wt stature (internal wild-type population) and cDNA 12482777 small stature (transgenic population).

| | Harvest Index: cDNA 12482777 Wt stature | Harvest Index cDNA 12482777 small stature |
|---|---|---|
| Mean | 44.91972222 | 56.9582619 |
| Variance | 42.68677253 | 89.40342666 |
| Observations | 6 | 10 |
| Hypothesized Mean Difference | 0 | |
| df | 14 | |
| t Stat | −3.004493678 | |
| P(T <= t) one-tail | 0.004733406 | |
| t Critical one-tail | 1.76130925 | |
| P(T <= t) two-tail | 0.009466812 | |
| t Critical two-tail | 2.144788596 | |

TABLE 3-44B

Statistical comparison of seed weight between transgenic population of clone 126592 and internal wild-type populations using a t-test on two samples assuming unequal variances. cDNA 12482777 Wt stature (internal wild-type population) and cDNA 12482777 small stature (transgenic population)

| | Seed Weight 12482777: WT stature | Seed Weight 12482777: Small Stature |
|---|---|---|
| Mean | 0.37155 | 0.30977 |
| Variance | 0.004473055 | 0.006150093 |
| Observations | 6 | 10 |
| Hypothesized Mean Difference | 0 | |
| df | 12 | |
| t Stat | 1.674926201 | |
| P(T <= t) one-tail | 0.059894848 | |
| t Critical one-tail | 1.782286745 | |
| P(T <= t) two-tail | 0.119789696 | |
| t Critical two-tail | 2.178812792 | |

Table 3-5 provides the results of the consensus sequence analysis based on Ceres cDNA 12482777 (CeresClone: 126592, SEQ ID NO:21). The amino acid of Clone:126592 (SEQ ID NO:21) is aligned with homologous and/or orthologous amino acid sequences CeresClone:278210 (SEQ ID NO:27) CeresClone:970125 (SEQ ID NO:24), CeresClone: 624535 (SEQ ID NO:25), gi|16974682 (SEQ ID NO:26), as well as with the consensus sequence (SEQ ID NO:61-79).

TABLE 3-5

```
CeresClone:278210  M- - - - - - - - -  - - - - - - - - - -  - - - - - - - - - -  - - - - - - - - - -  - - - - - - - - - -  - -         1
Lead•clone126592   MMNVAVTATP         SSLLYSPLLL         PS- - - - - -QG    PN- -RRMQWK        RNGKRRLGTK                   42
CeresClone:970125  MM- - - -MTTT      SSLLSPCSLL         PS- - - - - -QG    PN- -RQTQWK        RHEKRQFSRK                   38
CeresClone:624535  MNLSQSTAP          STSLSPSCFL         PR- - - -HPHG      STWFSSGTFK         FLKKESRCLR                   46
Gi|16974682        MKLLSPSATS         STHVSSAFL          PNVAGFQNLG         SS- -SVTTFK        FSKKQGRCIR                   48

Consensus          M- -LS-S-T-        S- -LS- - - -L     PS- - - - - - -G   - - - - - - - -K   -KK- - - - - -               50
```

TABLE 3-5-continued

```
CeresClone:278210  -----------  ----------  ----------  ----------  ----------  ----------    1
Lead•clone126592   VAVSGVITAG   FELKPPPYPL  DALEPHMSQE  TLDYHWGKHH  KTYVENLNKQ                92
CeresClone:970125  VVVSGVVRAG   FELKPPPYPL  DALEPHMSQE  TMDYHWGKHH  RTYVENLNKQ                88
CeresClone:624535  KAGRTKITAK   FELKPPPYPL  SALEPIMSRE  TLEYHWGKHH  RTYVDNLNRQ                96
Gi|16974682        RAGGTQITAK   FELKPPPYPL  NASEPIMSRN  TFEYHWGKHH  RAYVDNLNKQ                98

Consensus          -A----ITA-   FELKPPPYPL  -ALEP-MS-E  TL-YHWGKHH  RTYV-NLNKQ               100

CeresClone:278210  ---------S   LGOMMLASFN  EGREQPHPPF  FHAAQVWNHD  FYWRSMKPGG                42
Lead•clone126592   ILGTDLDALS   LEEVVLLSYN  KG--NMLPAF  NNAAQAWNHE  FFWESIQPGG               140
CeresClone:970125  ILGTDLDGLS   LEEVVLLSYN  RG--NMLPVF  NNAAQAWNHE  FFWESIQPGG               136
CeresClone:624535  IDGTDLDGNS   LENTIVITYN  KG--DILPAF  NNAAQAWNHD  FFWESMKPGG               144
Gi|16974682        IEGTDLDGKS   LEETIIMSYN  NG--DILPAF  NNAAQVWNHD  FFWESMKPGG               146

Consensus          I-GTDLDG-S   LEEV-LLSYN  KG----LPAF  NNAAQAWNHD  FFWESMKPGG               150

CeresClone:278210  GGKPPERLLK   FINRDFGSYE  GMIRQFMDAA  LTQFGSGWVW  LSYKGSGLPY                92
Lead•clone126592   GGKPTGELLR   LIERDFGSFE  EFLERFKSAA  ASNFGSGWTW  LAYKANRLDV               190
CeresClone:970125  GGKPSGDLLR   LIERDFGSFD  DF--------  ----------  ----------               158
CeresClone:624535  GGKPSGDLLN   LIERDFGTFE  KFLDEFKTAA  STQFGSGWAW  LAYKESRLDV               194
Gi|16974682        GGKPSGELLK   LIERDFGSFE  KFVEQFKLAA  STQFGSGWAW  LAYKESRLDV               196

Consensus          GGKPSG-LL-   LIERDFGSFE  -FIEQFK-AA  STQFGSGW-W  LAYK-SRLDV               200

CeresClone:278210  VKSRSPIPSD   NHGRLVLSKT  PNAINPLVWG  -HSPLLAIDV  WEHAYYLDYE               141
Lead•clone126592   ANAVNPLPKE   EDKKLVIVKT  PNAVNPLVWD  -YSPLLTIDT  WEHAYYLDFE               239
CeresClone:970125  ----------   ----------  ----------  ----------  ----------               158
CeresClone:624535  ENAVNPLQSD   EDKKLVVVKT  PNAVNPLVWN  YYHPLLTIDV  WEHAYFIDFQ               244
Gi|16974682        GNAVNPLATE   EDKKLVVLKS  PNAVNPLVWN  HHHPLLTIDV  WEHAYYLDYQ               246

Consensus          -NAVNPL-S-   EDKKLV-VKT  PNAVNPLVWN  ---PLLTIDV  WEHAYYLD--               250

CeresClone:278210  DRRADYVSAI   LEKLVSWETV  ESRLAKAVAR  AVERDEHLRR  RILRKQRLAQ               191
Lead•clone126592   NRRAEYINTF   MEKLVSWETV  STRLESAIAR  AVQREQE---  ---RTETEDE               283
CeresClone:970125  ----------   ----------  ----------  ----------  ----------               158
CeresClone:624535  NQRRDYISVF   MDKLVSWDAV  SSRLEQAKAL  IKEREREAER  K-RREEEEKR               293
Gi|16974682        NRRPEYISVF   MDKLVSWEAV  SSRLEKAKAV  IAEREKEEER  K-RREEEEKS               295

Consensus          NRR--YIS-F   M-KLVSWE-V  SSRLEKA-A-  --ERE-E--R  K--REE-E--               300

CeresClone:278210  ANGQSRARSR   ARQGRQGDQE  VARSRPVEA                                        220
Lead•clone126592   ENPDD-EVPE   VYLDSDIDVS  EVD------                                        305
CeresClone:970125  ----------   ----------  ---------                                        158
CeresClone:624535  TSSE--AIPE   IYSDGDADLD  AE-------                                        313
Gi|16974682        TTGEDTPAPE   IFADSDTD--  ---------                                        313

Consensus          ---E----PE   VY-D-D-D--  ---------                                        329
```

EXAMPLE 4

Ceres cDNA 12333678

Clone 26006, Ceres cDNA 12333678, encodes a full-length glycosyl hydrolase. Ectopic expression of Ceres cDNA 12333678 under the control of the CaMV35S promoter induces the following phenotypes:

Germination on high concentrations of polyethylene glycol (PEG), mannitol and abscissic acid (ABA).

Continued growth on high PEG, mannitol and ABA.

Generation and Phenotypic Evaluation of $T_1$ Lines Containing 35S::cDNA 12333678.

Wild-type *Arabidopsis* Wassilewskija (WS) plants were transformed with a Ti plasmid containing cDNA 12333678 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance.

Seeds from 13 superpools (1,200 $T_2$ seeds from each superpool) from the CaMV35S or 32449 over-expression lines were tested on high pH media as described above. $T_3$ seeds were collected from the tolerant plants and analyzed for tolerance on all additional high pH screens.

Once cDNA 12333678 was identified in tolerant plants, the individual $T_2$ events containing this cDNA (ME01334) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Results:

Qualitative Assessment of ME01334 on High pH.

Superpool 1 was screened on high pH media as described above. PCR analyses identified ME01334 as one of the ME lines showing high pH resistance. Testing of the second generation confirmed the inheritance of the pH resistance (data not shown).

ME01334 plants that recovered after high pH produced an exceptionally large number of seeds compared to wild-type controls. Additional testing confirmed that these plants statistically produce 30-80% more seeds than either wild-type or transgenic control plants that are recovered from this screen or transferred from regular MS media.

Table 4-1 provides the results of the consensus sequence analysis based on Ceres cDNA 12333678 (CeresClone: 26006, SEQ ID NO:31). The amino acid of Clone 26006 (SEQ ID NO:31) is aligned with homologous and/or orthologous amino acid sequences gi|5866583 (SEQ ID NO:48), gi|2780225 (SEQ ID NO:38), gi|50513520 (SEQ ID NO:36) gi|6435646 (SEQ ID NO:37), gi|57899620 (SEQ ID NO:47), CeresClone:936068 (SEQ ID NO:45), gi|34907176 (SEQ ID NO:46), gi|56393011 (SEQ ID NO: 49) gi|4814856 (SEQ ID NO:41), gi|56392765 (SEQ ID NO:43), CcresClone:644331 (SEQ ID NO:44), gi|53830670 (SEQ ID NO:39), Ceres-Clone:1010900 (SEQ ID NO:33), gi|20196998 (SEQ ID NO:34), gi|27754457 (SEQ ID NO:35), gi|6651393 (SEQ ID NO:40), gi|4279437 (SEQ ID NO:32), gi|40549303 (SEQ ID NO:42), as well as with the consensus sequence (SEQ ID NO:80-96).

TABLE 4-1

```
gi|15866583        MGGDGGAEQP  VIHFVFVHGA  SHGAWCWYKL  TSLLETAGFK  TTSVDLTGAG  50
gi|2780225         --------MA  VVDFVLIHTI  CHGAWIWYKL  KPVLEAAGHK  VTALDLAASG  42
gi|50513520        --------MA  FAHFVLIHTI  CHGAWIWHKL  KPLLEALGHK  VTALDLAASG  42
gi|6435646         --------MA  FAHFVLIHTI  CHGAWIWYKL  KPLLEALGHK  VTALDLAASG  42
gi|57899620        ---MEGSSSS  SKHFILIHGL  CHGAWCWYKV  VTMLRSEGHR  VTALDLAASG  47
CeresClone:936068  ----MEGSSS  GKHFILIHGL  CHGAWCWYKL  VPMLRAAGHR  VTALDMAASG  46
gi|34907176        ---MEISSSS  KKHFILIHGL  CHGAWCWYRV  VAALRAAGHR  ATALDMAASG  47
gi|56393011        -MEKSMSPFV  KKHFVLVHTA  FHGAWCWYKI  VALMRSSGHN  VTALDLXASG  49
gi|41814856        -----MEKGD  KNHFVLVHGA  CHGAWCWYKV  VTILRSEGHK  VSVLDMAASG  45
gi|56392765        -----MEKGN  KNHFVLVHGA  CHGAWCWYKV  VTILRSEGHK  VSVLDMAASG  45
CeresClone:644331  -MEACAGQAS  SAHIVLVHGA  CLGGWSWFKV  ATRLRSAGHR  VSTPDLAASG  49
gi|53830670        -------MEV  MKHFVTVHGV  GHGAWVYYKL  KPRIEAAGHR  CTAVNLAASG  43
Lead•clone26006    ----MSEEKR  KQHFVLVHGA  CHGAWCWYKV  KPLLEALGHR  VTALDLAASG  46
CeresClone:1010900 ----MSEEKR  KQHFVLVHGS  CHGAWCWYKV  KPLLEAVGHR  VTAVDLAASG  46
gi|20196998        ----MSEEKR  KQHFVLVHGS  CHGAWCWYKV  KPLLEAVGHR  VTAVDLAASG  46
gi|27754457        ----MSEEKS  KQHFVLVHGS  CHGAWCWYKV  KPLLEAVGHR  VTAVDLAASG  46
gi|6651393         -MHSAANAKQ  QKHFVLVHGG  CLGAWIWYKL  KPLLESAGHK  VTAVDLSAAG  49
gi|14279437        --MEEVVGME  EKHFVLVHGV  NHGAWCWYKL  KARLVAGGHR  VTAVDLAASG  48
gi|40549303        -------MKE  GKHFVLVHGA  CHGGWSWYKL  KPLLEAAGHK  VTALDLAASG  43

Consensus          ----------  KKHFVLVHGA  CHGAWCWYK-  KPLLEA-GHR  VTALDLAASG  50 gi|15866583        IS-VTDSNTV  LESDQYNRPL  FSLLSDLPP-  SHKVILVGHS  IGGGSVTDAL  98
gi|2780225         VD-PRQIEQI  NSFDEYSEPL  LTFMESLPQ-  GEKVILVGES  CGGLNIAIAA  90
gi|50513520        VD-PRQIEEI  GSFDEYSEPL  LTFLEALPP-  GEKVILVGES  CGGLNIAIAA  90
gi|6435646         VD-PRQIEEI  GSFDEYSEPL  LTFLEALPP-  GEKVILVGES  CGGLNIAIAA  90
gi|57899620        VH-PARVDEV  HSFEEYSQPL  LDAVAEAPA-  GERLILVGHS  FGGLSIALAM  95
CeresClone:936068  AH-PARMDEV  PSFEDYSWPL  LDAVAAAPA-  GERLVLVGHS  LGGLNIALAM  94
gi|34907176        AH-PARVDEV  GTFEEYSRPL  LDAVAAAAAP  HGGLSVALAS  HGGLSVALAS  96
gi|56393011        IN-PKQALQI  PNFSDYLSPL  MEFMASLPA-  NEKIILVGHA  LGGLAISKAM  97
gi|41814856        IN-PKHVDDL  NSMADYNEPL  MEFMNSLPQ-  LERVVLVGHS  MGGINISLAM  93
gi|56392765        IN-PKHVEDL  NSMANSMPGP  MEFMNSLPQ-  QERVVLVGHS  MGGINISLAM  93
CeresClone:644331  VD-PRPLREV  PTFRDYTKPL  LDLLESLPS-  GEKVILVGHS  LGGVNVALAC  97
gi|53830670        IN-EKKLEEV  RSSIDYAAPL  LEVLDSVPE-  NEKVILVGHS  GGGMTAAVGM  91
Lead•clone26006    IDTTRSITDI  STCEQYSEPL  MQLMTSLPN-  DEKVVLVGHS  FGGLSLALAM  95
CeresClone:1010900 IDTTRSITDI  PTCEQYSEPL  TKLLTSLPN-  DEKVVLVGHS  FGGLNLAIAM  95
gi|20196998        IDTTRSITDI  PTCEQYSEPL  TKLLTSLPN-  DEKVVLVGHS  FGGLNLAIAM  95
gi|27754457        IDTTRSITDI  PTCEQYSEPL  TKLLTSLPN-  DEKVVLVGHS  FGGLNLAIAM  95
gi|6651393         IN-PRRLDEI  HTFRDYSEPL  MEVMASIPP-  DEKVVLVGHS  FGGMSLGLAM  97
gi|14279437        IN-MKRIEDV  HTFHAYSEPL  MEVLASLPA-  EEKVILVGHS  LGGVTLALAG  96
gi|40549303        TD-LRKIEEL  RTLYDYTLPL  MELMESLSA-  DEKVILVGHS  LGGMNLGLAM  91

Consensus          I--PRQI-EI  --FE-YSEPL  MELM-SLP--  -EKVVLVGHS  -GGLNIALAM  100 gi|15866583        CRFTDKISMA  IYLAASMVKP  GSVPSPHVSD  MHADAREEN-  IW---EYTYG  144
gi|2780225         DKYPEKIAAA  VFQNSLLPDT  KHKPSYVVDK  LMEVFPD---  -WKDTEYFEF  136
gi|50513520        DKYCEKIAAA  VFHNSVLPDT  EHCPSYVVDK  LMEVFPD---  -WKDTTYFTY  136
gi|6435646         DKYCEKIAAA  VFHNSVLPDT  EHCPSYVVDK  LMEVFPD---  -WKDTTYFTY  136
gi|57899620        ERFPEKIAVA  VFVAAAVPCV  GKR--IIPEL  IREKAPKDM-  -LLDSKMIPI  141
CeresClone:936068  ERFPRKVAAA  VFLAACMPCV  GRHMGATTEE  IMRRIKPDF-  -FMDMKRMVL  142
gi|34907176        ERFPDKVAAA  VFVAAAMPCV  GKHMGVPTEE  FMRRTAPEG-  LLMDCEMVAI  145
gi|56393011        ETFPEKISVA  VFLSGLMPGP  NIDATTVCTK  AGSAVLG---  -QLDNCVTYE  143
gi|41814856        EKFPQKIVVA  VFVTAFMPGP  DLNLVALGQQ  YNQQVES---  -HMDTEFVYN  139
gi|56392765        EKFPWHSMPGP  VFVSASMPGP  DLNLVAIVQQ  YSQQVET---  -PMDTEFVYN  139
CeresClone:644331  ELFPEKIAAA  VFVAAFMPDH  RSPPSYVLEK  FVEGRTLD--  -WMDTEFKPQ  144
gi|53830670        EKFPNKISLA  VFLNAIMPDT  ENRPSYVLEE  YTAKTPPEA-  -WKDCQFSAY  139
Lead•clone26006    DKFPDKISVS  VFVTAFMPDT  KHSPSFVEEK  FASSMTPEG-  -WMGSELETY  143
CeresClone:1010900 EKFPEKISVA  VFLTAFMPDT  EHSPSFVLDK  FGSNMPQEA-  -WMGTEFEPY  143
gi|20196998        EKFPEKISVA  VFLTAFMPDT  EHSPSFVLDK  FGSNMPQEA-  -WMGTEFEPY  143
gi|27754457        EKFPEKISVA  VFLTAFMPDT  EHSPSFVLDK  FGSNMPQEA-  -WMGTEFEPY  143
gi|6651393         ETYPEKISVA  VFMSAMMPDP  NHSLTYPFEK  YNEKCPADM-  -MLDSQFSTY  145
gi|14279437        DKFPHKISVA  VFVTAFMPDT  THRPSFVLEQ  YSEKMGKEDD  SWLDTQFSQC  146
gi|40549303        EKYPQKIYAA  VFLAAFMPDS  VHNSFVLEQ  YNERTPAEN-  -WLDTQFLPY  139

Consensus          EKFPEKISVA  VFL-A-MPDT  EH-PS-VLEK  -----P-E--  -WMDTEF--Y  150
```

TABLE 4-1-continued

```
gi|15866583        EG-TDKPPTG  VIMKQEFLRQ  YYYSQSPLED  VSLATKLLRP  APMRAFQDLD   193
gi|2780225         SNSNGETITG  MVLGLKLMRE  NLYTICPPED  YELAKMLTRR  GSLFQSI-LA   185
gi|50513520        TK-DGLEITG  LKLGFTLLRE  NLYTLCGPEE  YELAKMLTRK  GSLFQNI-LA   184
gi|6435646         TK-DGLEITG  LKLGFTLLRE  NLYTLCGPEE  YELAKMLTRK  GSLFQNI-LA   184
gi|57899620        NN-KQGPGTA  ILLGPNFLAE  KGYPLSPAED  LTLAKLLVRP  TSQFVDDPTM   190
CeresClone:936068  NT-SQGPRPA  LVFGPKILAA  KLYDRSSGED  QTLATMLVRP  GCQFLDDPTM   191
gi|34907176        NN-SQGSGVA  INLGPKFLAQ  KYYQQSPAED  LALAKMLVRP  GNQFMDDPVM   194
gi|56393011        NG-PTNPPTT  LIAGPKFLAT  NVYHLSPIED  LALATALVRP  LYLYLAEDIS   192
gi|41814856        NG-QDKAPTS  LVLGPEVLAT  NFYQLSPPED  LTLATYLVRP  VPLFDESILL   188
gi|56392765        NG-LDKPPTS  VVLGPKVLAT  IYYQFSPPED  LTLATYLVRP  VPLFDESVLL   188
CeresClone:644331  DP-EGDLPTS  MLFGPLVTRA  KFFQLCSPED  LTLGRSLMRV  NSMFVDD-LR   192
gi|53830670        G---DPPITS  LVCGPEFISS  TLYHLSPIED  HALGKILVRP  GSLFIED-LL   185
Lead•clone26006    G---SDNSGLS  VFFSTDFMKH  RLYQLSPVED  LELGLLLKRP  SSLFINE-LS   190
CeresClone:1010900 G---SDNSGLS  MFFSPDFMKL  GLYQLSPVED  LELGLLLMRP  GSLFIND-LS   190
gi|20196998        G---SDNSGLS  MFFSPDFMKL  GLYQLSPVED  LELGLLLMRP  GSLFIND-LS   190
gi|27754457        G---SDNSGLS  MFFSPDFMKL  GLYQLSPVED  LELGLLLMRP  GSLFIND-LS   190
gi|6651393         GN-PENPGMS  MILGPQFMAL  KMFQNCSVED  LELAKMLTRP  GSLFFQD-LA   193
gi|14279437        DA-SNPSHIS  MLFGREFLTI  KIYQLCPPED  LELAKMLVRP  GSMFIDN-LS   194
gi|40549303        GS-PEEPLTS  MFFGPKFLAH  KLYQLCSPED  LALASSLVRP  SSLFMED-LS   187

Consensus          --------TS  MI-GP-FL--  -LYQLSP-ED  L-LA-MLVRP  GSLFI-D-LS   200 gi|15866583        KSPP---NPE  VEKVPRVYIK  TGKDNLFSSV  -RQDLLVKNW  PPSQFYVLEE   239
gi|2780225         QREK-FTRKG  YGSIKKIYVW  TGDDKIFLPE  -FQLWQIENY  PKDLVFRVMG   233
gi|50513520        KRPF-FTKEG  YGSIKKIYVW  TDQDEIFLPE  -FQLWQIENY  KPDKVYKVEG   232
gi|6435646         KRPF-FTKEG  YGSIKKIYVW  TDQDEIFLPE  -FQLWQIENY  KPDKVYKVEG   232
gi|57899620        KDDRLLTSAN  YGSVKRVCLM  AMEDDL--KE  -VHRYMITLS  PGVEVEEIAG   237
CeresClone:936068  KDEALLTEAK  YGSVKKVYVV  AMADASNSEE  -MQRWMVDMS  PGTEAEEIAG   240
gi|34907176        KDESLLTNGN  YGSVKKVYVV  AKADSSSTEE  -MQRWMVAMS  PGTDVEEIAG   243
gi|56393011        KEVV-LSSKR  YGSVKRVFIV  ATENDALKKE  -FLKLMIEKN  PPDEVKEIEG   240
gi|41814856        ANTT-LSKEK  YGSVHRVYVV  CDKDNVLKEQ  QFQKWLINNN  PPDEVQIIHN   237
gi|56392765        TNTT-LSKEK  YGSVHRVYVV  CDKDVLKEE   QFQRWLIKNN  PPNEVQMIHD   237
CeresClone:644331  LQPP-HTEAR  YGSVRKAYVV  FKDDHAIVEQ  -FQRWMVHNY  PVDEVMEIDG   240
gi|53830670        KAEK-FTEEG  FGSVPRVYVI  AAEDKTIPPE  -FQRWMIENN  PVKEVKEIKG   233
Lead•clone26006    KMEN-FSEKG  YGSVPRAYIV  CKEDNIISED  -HQRWMIHNY  PANLVIEMEE   238
CeresClone:1010900 KMKN-FSDEG  YGSVPRVFIV  CKEDKAIPEE  -RQRWMIDNF  PVNLVMEMEE   238
gi|20196998        KMKN-FSDEG  YGSVPRVFIV  CKEDKAIPEE  -RQRWMIDNF  PVNLVMEMEE   238
gi|27754457        KMKN-FSDEG  YGSVPRVFIV  CKEDKAIPEE  -RQRWMIDNF  PVNLVMEMEE   238
gi|6651393         KAKK-FSTER  YGSVKRAYIF  CNEDKSFPVE  -FQKWFVESV  GADKVKEIKE   241
gi|14279437        KESK-FSDEG  YGSVKRVYLV  CEEDIGLPKQ  -FQHWMIQNY  PVNEVMEIKG   242
gi|40549303        KAKY-FTDER  FGSVKRVIYV  CTEDKGIPEE  -FQRWQIDNI  GVTEAIEIKG   235

Consensus          K----F--E-  YGSVKRVYIV  --ED--I-EE  -FQRWMIENY  P--EV-EIEG   250 gi|15866583        SDHSAFFSVP  TTLFVYLLRA  VSFLHK                              265
gi|2780225         GDHKLQLTKT  NEIAGILQKV  ADIYA-                              258
gi|50513520        GDHLLQLTKT  KEIAEILQEV  ADTYN-                              257
gi|6435646         GDHKLQLTKT  KEIAEILQEV  ADTYN-                              257
gi|57899620        ADHAVMCSRP  RELSDLLAKI  GSKYD-                              262
CeresClone:936068  ADHMAMCSKP  RELCDVLLRI  ADKYE-                              265
gi|34907176        ADHAVMNSKP  RELCDILIKI  ANKYE-                              268
gi|56393011        SDHVTMMSKP  QQLFTTLLSI  ANKYK-                              265
gi|41814856        ADHMVMFSKP  RDLSSCLVMI  SQKYY-                              262
gi|56392765        AGHMVMFSKP  RELCSCLVMI  SQKYH-                              262
CeresClone:644331  ADHMALLSTP  TELARCLADI  AVKYAA                              266
gi|53830670        ADHMPMFSKP  DELSQCLLDI  AKKHA-                              258
Lead•clone26006    TDHMPMFCKP  QVLSDHLLAI  ADNFS-                              263
CeresClone:1010900 TDHMPMFCKP  QQLSDYFLKI  ADKFV-                              263
gi|20196998        TDHMPMFCKP  QQLSDYFLKI  ADKFV-                              263
gi|27754457        TDHMPMFCKP  QQLSDYFLKI  ADKFV-                              263
gi|6651393         ADHMGMLSQP  REVCKLLDI   SDS---                              264
gi|14279437        GDHMAMLSDP  QKLCDCLSQI  SLKYA-                              267
gi|40549303        ADHMAMLCEP  QKLCASLLEI  AHKYN-                              260

Consensus          -DHM-M-SKP  QELS--LL-I  A-KY--                              276
```

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A method for increasing pH tolerance or phosphate use efficiency in a plant comprising
   (1) transforming a plant with a recombinant DNA construct comprising a nucleic acid encoding a pH tolerance or phosphate use efficiency component operably linked to a plant promoter so that the pH tolerance or phosphate use efficiency component is ectopically overexpressed in the transgenic plant and
   (2) selecting a transgenic plant that exhibits:
   i) higher tolerance to high pH,
   ii) higher tolerance to low phosphate concentration, or
   iii) higher tolerance to low nitrogen concentration than a progenitor plant which does not contain the construct, when the transgenic plant and the progenitor plant are cultivated under identical environmental conditions, and wherein the pH or phosphate use efficiency component is a polypeptide comprising the amino acid sequence of SEQ ID NO:2.

2. A transgenic plant having a recombinant DNA construct comprising a nucleic acid encoding a pH tolerance or phosphate use efficiency component operably linked to a plant promoter so that the pH tolerance or phosphate use efficiency component is ectopically overexpressed in the transgenic plant, and the transgenic plant exhibits:
   i) higher tolerance to high pH,
   ii) higher tolerance to low phosphate concentration, or
   iii) higher tolerance to low nitrogen concentration than a progenitor plant which does not contain the construct, when the transgenic plant and the progenitor plant are cultivated under identical environmental conditions, and wherein the pH or phosphate use efficiency component is a polypeptide comprising the amino acid sequence of SEQ ID NO:2.

3. A plant cell, plant material or seed obtained from the transgenic plant of claim 2, wherein the plant cell, plant material or seed comprises the recombinant DNA construct.

* * * * *